US006524588B1

(12) United States Patent
Hobom et al.

(10) Patent No.: US 6,524,588 B1
(45) **Date of Patent: *Feb. 25, 2003**

(54) ATTENUATED VACCINATION AND GENE-TRANSFER VIRUS, A METHOD TO MAKE THE VIRUS AND A PHARMACEUTICAL COMPOSITION COMPRISING THE VIRUS

(75) Inventors: Gerd Hobom, Arndtstrasse 14, D 35392 Giessen (DE); Gabriele Neumann, Maintal (DE); Annette Menke, Marburg (DE)

(73) Assignee: Gerd Hobom, Giessen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,513

(22) Filed: Mar. 24, 1997

Related U.S. Application Data

(63) Continuation of application No. PCT/EP95/03663, filed on Sep. 18, 1995, now abandoned.

(30) Foreign Application Priority Data

Sep. 30, 1994 (EP) .......................................... 94115505

(51) Int. Cl.[7] ...................... A61K 39/12; A61K 39/145

(52) U.S. Cl. .............................. 424/208.1; 424/184.1; 424/188.1; 424/204.1; 424/206.1; 424/220.1; 435/69.1; 435/91.1; 435/172.3; 435/235.1; 435/69.3

(58) Field of Search .............................. 435/69.1, 91.1, 435/172.3, 235.1, 69.3; 424/184.1, 188.1, 204.1, 206.1, 199.1, 220.1

(56) References Cited

U.S. PATENT DOCUMENTS 5,166,057 A * 11/1992 Palese et al. ............. 435/69.1

OTHER PUBLICATIONS

Seong, et al.: Nucleotides 9 to 11 of the influenza . . . : J. Gen. Vir.: 73: pp. 3115–3124, 1992.*

Luytjes, et al.: Amplification, expression, and packaging of a . . . : Cell: vol. 59: pp. 1107–1113, Dec. 1989.*

Dogget, et al.: Immune responses to streptococcis . . . : Inf. and Imm. : pp. 1859–1866, May 1993.*

Carrasco, L. et al. 'Regulation of gene expression in animal viruses'; 1993, Plenum Press, New York pp. 107–114, Garcia–Sastre, A & Palese, P.: 'Infectious influenza viruses from cDNA–derived RNA; reverse genetics'.

Cell, vol. 59, no. 6, Dec. 22, 1989, Cambridge, NA US pp. 1107–1113, Luytjes, W. et al. 'Amplification, expression, and packaging of a foreign gene by influenza virus'

Journal of Virology, vol. 67, No. 11, pp. 6659–6666, Li, et al. 'Chimeric influenza virus induces neutralizing antibodies and cytotoxic T cells against human immunodeficiency virus type 1' (1993). .

J Virol 66 (7). 1992. 4331–4338, Li, X. et al. 'Mutational analysis of the promoter required for fluenza virus virion RNA synthesis'.

Virus Res 28 (2). 1993. 99–112, Piccone, M. et al. 'Mutational analysis of the influenza virus VRNA promoter'.

Journal of virology, vol. 68, No. 6, pp. 4092–4096, Fodor, E. et al. 'The influenza virus panhandle in involved in the initiation of transcription' (1994).

Journal of general virology 76 (7). 1709–1717, Jul. 1995, Neumann, G. et al. 'Mutational analysis of influenza virus promotor elements in vivo'.

Fall Meeting of the Society of Biological Chemistry, Wuerzburg, Germany, Sep. 19–21, 1994. Biological Chemistry Hoppe–Seyler 375 (Spec. Suppl. 1) 1994. S73, XP 000561852, Menke, A. et al. 'Ribozyme mediated cleavage of influenza NP–vRNA in vitro and in vivo'.

Keystone Symposium on Ribozymes; Basic Science and Therapeutic applications, Breckenridge, Colorado, USA, Jan. 15–21, 1995. Journal of Cellular Biochemistry Supplement 0 (19A). 1995, 223, Menke, A. et al. 'Double ribozyme mediated cleavage of influenza A NP–vRNA'.

J Med Virol, (Apr. 1994) 42 (4) 385–95, XP 000561857, Tang, X. et al. 'Ribozyme mediated destruction of influenza A virus in vitro and in vivo'.

* cited by examiner

*Primary Examiner*—Mary E. Mosher
*Assistant Examiner*—Myron G. Hill
(74) *Attorney, Agent, or Firm*—Norris McLaughlin & Marcus

(57) ABSTRACT

RNA polymerase I transcription in vivo in transiently DNA-transfected cells has been used for expression of influenza vRNA molecules coding for chloramphenicol acetyltransferase (CAT) in anti-sense orientation. Influenza virus superinfection served to provide viral RNA polymerase and other proteins for transcriptional conversion of minus-strand vRNA into plus-strand viral mRNA molecules expressing CAT activity. This system has been used for an analysis via nucleotide exchanges as well as deletions and insertions of both terminal segments of the vRNA sequence which cooperatively constitute the vRNA promoter structure. Several mutants with greatly enhanced expression rates over wild-type levels have been constructed, which also can be packaged and serially passaged into progeny virus. The data obtained for the mutations in various promoter elements support a model of consecutive, double strand vRNA promoter structures in binding of viral polymerase and initiation of RNA synthesis. Preparations of attenuated influenza virus for vaccination purposes include a single recombinant segment with promoter up mutation(s) for over-expression of an own or foreign gene product, which at the same time because of its over-replication serves to decrease the number of helper virus RNP segments. The same viruses further have been passaged through a step of ribozyme cleavage acting at one of the helper viral segments, which will delete this vital function and structure with high rates from the virus progeny. The resulting attenuated viruses will interact with their target cells in only one round of abortive infection, and are unable to produce viral progeny.

13 Claims, 3 Drawing Sheets

Figure 1A:
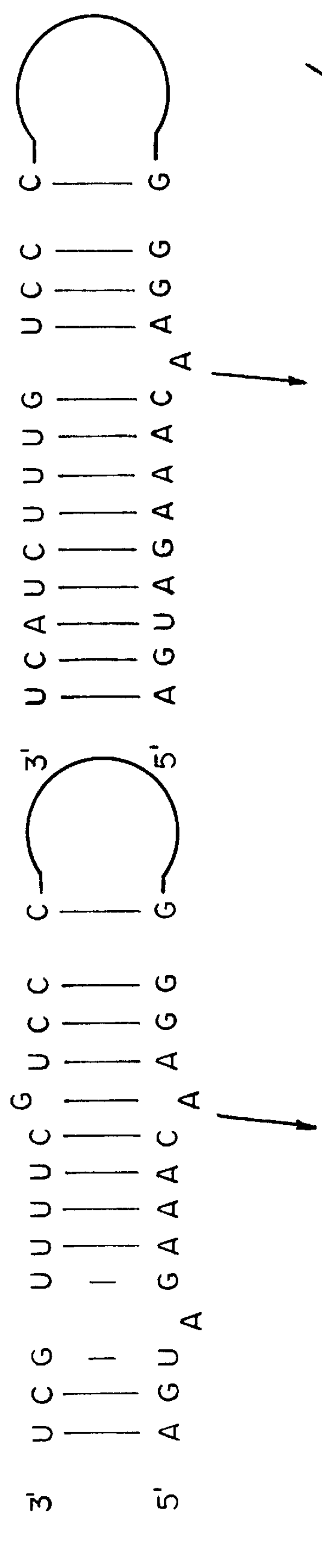

WILD TYPE vRNA PROMOTER STRUCTURE pHL 1104 DERIVED MUTANT vRNA PROMOTER STRUCTURE

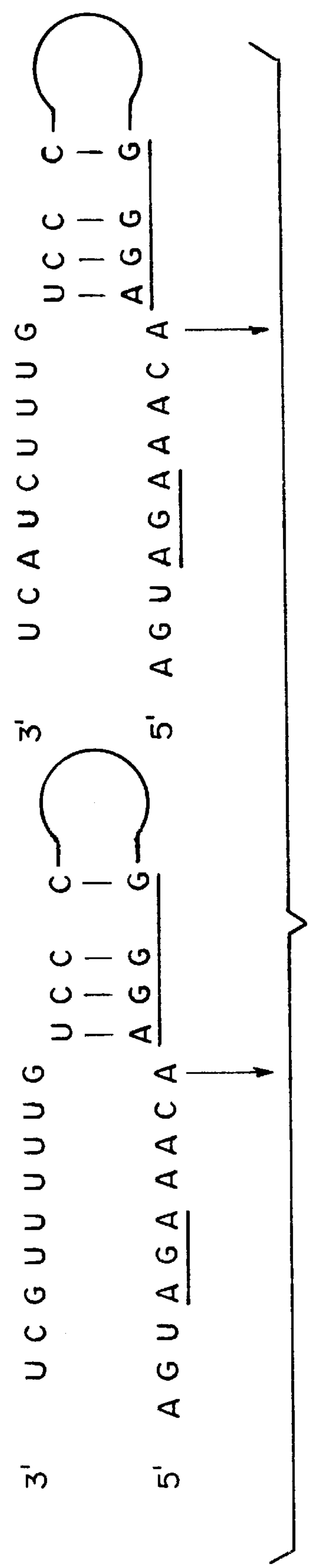
FIG.IC
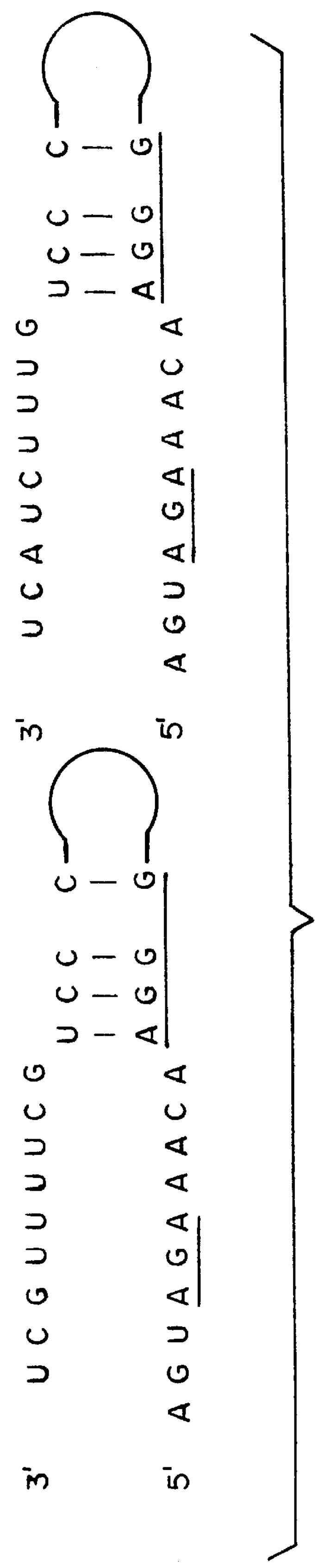
FIG.ID

ATTENUATED VACCINATION AND GENE-TRANSFER VIRUS, A METHOD TO MAKE THE VIRUS AND A PHARMACEUTICAL COMPOSITION COMPRISING THE VIRUS

This is a continuation of international application PCT/EP95/03663, filed Sep. 18, 1995, which designated the United States and is now abandoned.

The object of the present invention was to make a vaccination virus. This objective has been fulfilled with the segmented virus constructed as described herein.

The genome of influenza A viruses consists of 8 different single-stranded viral RNA (vRNA) molecules of negative polarity, which have in common 5' and 3' terminal sequences largely complementary to each other. These conserved segments 13 and 12 nucleotides in length are known to form double-stranded RNA panhandle structures (Hsu et al., 1987; Fodor et al., 1993) which have been analysed in more detail recently in vitro using internally deleted model RNAs (Baudin et al., 1994; Tiley et al., 1994). In the virion the panhandle ends of all RNA segments are found in specific binding to viral RNA polymerase complexes, while the remaining internal segments stay single-stranded with viral nucleoprotein (NP) in cooperative binding (Compans et al., 1972; Honda et al., 1988; Martin et al., 1992). Upon infection these viral RNPs initially serve as templates for the synthesis of viral mRNAs by a specific cap-snatching mechanism (Plotch et al., 1979; Braam et al., 1983), and later on will direct synthesis of full-length complementary RNAs (cRNAs), probably dependent on the absence or presence of newly synthesized NP protein (Shapiro and Krug, 1988). The plus-strand cRNAs are then used as templates for progeny vRNA synthesis.

The viral RNA polymerase complex consisting of proteins PB1, PB2, and PA is involved in all three different modes of RNA synthesis during the viral replication cycle, following its specific binding to the terminal panhandle segments of both vRNAs and cRNAs. Sequence comparison reveals that the vRNA and cRNA termini have similar, but not identical sequences. For that reason vRNA and cRNA recognition may be distinguished because of these structural alterations allowing for asymmetries in initiation of plus and minus strand RNA synthesis, and possibly in viral RNP packaging, which has also been suggested to be controlled by the panhandle RNA sequence (Hsu et al., 1987).

Recently, we reported on an in vivo system for the introduction of specific mutations into the genome of influenza viruses: viral cDNA has been inserted in antisense orientation between mouse rDNA promoter and terminator sequences.

This has been derived from in vitro transcription experiments based on nuclear extracts from Ehrlich ascites cells, which resulted in transcripts exactly resembling influenza vRNA. For a series of in vivo studies, the viral coding sequence was replaced by the coding sequence for chloramphenicol-acetyltransferase (CAT), however, with both influenza terminal non-coding sequences being retained exactly on the resulting vRNA transcripts. After transfection of this recombinant DNA template into mouse cells followed by influenza virus infection, CAT activity was detectable. Transfer of supernatants to different cells demonstrated that CAT-vRNAs transcribed in vivo by cellular RNA polymerase I were not only transcribed by viral RNA polymerase into plus-strand mRNA and translated into CAT protein, but also were replicated and packaged into infectious progeny virus particles (Zobel et al., 1993; Neumann et al., 1994).

We have used this system for a stepwise introduction of single and multiple mutations into the conserved panhandle RNA sequence, thereby effectively converting the HA-vRNA promoter sequence into an HA-cRNA promoter sequence and vice versa. For these series of constructs CAT activities have been measured both in primarily transfected and infected B82 cells and, after passaging of B82 supernatants, in secondarily infected MDCK cells. From the results obtained we propose a model for the terminal RNA sequence as being recognized RNA polymerase in consecutive steps of different structure when used as a template for initiation of viral mRNA synthesis.

The present invention relates to a segmented RNA virus which comprises one or more segments which have been genetically modified to show improved transcription, replication and/or expression rates.

The virus can be one where one or more modifications have been introduced in the noncoding region(s) and/or one or more modifications have been introduced in the coding region(s). A possibility is that at least one modified segment is derived from an original one by sequence variation(s). It is also possible that at least one modified segment is an artificial addition to the set of original or modified original segments. The virus can be one wherein the modified segment comprises a nucleotide sequence which codes for a protein or peptide which is foreign to the original virus. Preferred is that the foreign protein or peptide constitutes an antigen or antigen-like sequence, a T-cell epitope or related sequence. In such a case it is possible that the segment comprises repetitions of an antigen or epitope or other. Such an antigen or epitope can be for example derived from HIV, Herpes-Virus, Human Papilloma virus, Rhinovirus, CMV or Hog Cholera Virus (HCV). The virus of the present invention may be a single stranded negative-strand RNA virus as for example one of the Orthomyxoviridae family, the Bunyaviridae family or of the Arenaviridae family. The most preferred virus is an influenza virus. The virus of the present invention can also be a double-stranded RNA virus, as for example a reovirus, a rotavirus or an orbivirus. The viruses of the present invention can be used in gen-therapy.

The present invention also relates to the virus and use of the virus for the preparation of pharmaceuticals.

Mutational Analysis of vRNA 3' Terminal Sequence Positions.

Influenza A viral RNA 5' and 3' ends have similar, but not identical sequences with nucleotide mismatches at positions 3, 5 and 8, and an additional unpaired nucleotide is located at position 10 in the 5' region. Nevertheless, both vRNA termini hybridize into a double stranded panhandle structure made up of twelve and thirteen nucleotides in common for all eight RNA segments, plus in average three additional basepairs specific for each of the vRNA molecules. Due to the deviations mentioned the cRNA or plus strand panhandle structures have to be different from the vRNA structures; however, both are recognized by viral RNA polymerase and are used for initiation of RNA synthesis, i.e. they are constituting a promoter structure. Even if in initial recognition and binding of RNA polymerase the double stranded RNA panhandle structure is known to be the substrate, and is also observed in virion RNPs (Hsu et al., 1987), for the initiation step of transcription at the 3' ultimate template position this terminal region has to be separated into a partially single stranded, i.e. 'forked' structure (Fodor et al., 1994). RNA polymerase may be predicted to continue its binding interaction with both, the remaining double stranded segment: nucleotides $\overline{10}$ to $\overline{15}$versus 11 to 16[1], and to the-single stranded 3' template segment: nucleotides $\overline{1}$up to $\overline{9}$, as well as the 5' single stranded end (Tiley et al., 1994). Introduction of mutations at specific positions in either strand may hence alternate simultaneously both of these consecutive vRNA promoter structures: panhandle and fork in different ways, and will in addition also result in corresponding variations of the cRNA promoter structure.

Notations concerning nucleotides $\overline{1}$to $\overline{15}$ refer to positions in the vRNA 3' end, e.g. position 2 designates the penultimate nucleotide; 5' end positions are given in ordinary numbers. The notation $G\overline{3}A$ describes a mutational change of guanosine to adenosine at position $\overline{3}$.

To investigate the importance of the three mismatch positions, specific single, double or triple nucleotide exchanges were first introduced into the vRNA 3' end sequence at positions $\overline{3}$, $\overline{5}$ and $\overline{8}$, thereby approaching a fully double-stranded vRNA promoter structure, in a step-wise manner. At the same time the vRNA 3' end template sequence will become equivalent to the cRNA 3' end in these positions, but not in regard to the additional nucleotide at position 10. Single nucleotide exchanges according to this scheme (pHL1098, pHL1099, pHL1100) abolished the promoter activity, and no CAT activity was observed, as has been reported before with a different method (Luo et al., 1993). Two of the double mutation constructs (pHL1101, pHL1103) also gave negative results.

In contrast, for pHL1102 (G3A, U8C)[1], a significant CAT activity was detected, distinctly higher than for the corresponding wild-type construct (pHL926;) which in the conditions applied (8 hr after infection) resulted in rather low levels of CAT expression. This activity increase is further enhanced for the final construct of this series carrying the triple exchange $G\overline{3}A$, CSU and $U\overline{8}C$ (pHL1104), i. e. trans-fection of pHL1104 DNA followed by influenza virus infection resulted in a very high level of CAT expression, also considerably above the pHL1102 results.

[1]Notations concerning nucleotides$\overline{1}$ to $\overline{15}$ refer to positions in the vRNA 3' end, e.g. position $\overline{2}$ designates the penultimate nucleotide; 5' end positions are given in ordinary numbers. The notation $G\overline{3}A$ describes a mutational change of guanosine to adenosine at position $\overline{3}$.

These results have been repeated using various conditions of transfection and infection as well as determining kinetic data during the course of infection. While the pHL1104 variant is always observed far superior over any wild-type construct that expression ratio may be variable and difficult to quantitate (between around 20 fold and nearly 100 fold). Rather short infective cycles of eight hours as used prevalently appear to put more slowly replicating, i.e. wild-type molecules at a disadvantage, in particular in passaging of packaged pseudo-vRNA molecules via virus progeny, both is found increased for wild-type and related constructs after DNA transfection plus twelve hours of infection (see Neumann et al., 1994). Remaining deviations in CAT expression ratios may be attributed to variations in growth conditions in individual experiments.

Mutational Analysis of vRNA 5' Terminal Sequence Positions

We also addressed the question whether the unexpectedly high viral mRNA expression rate of pHL1104 is the consequence of a stabilized panhandle double-strand structure or may be directly attributed to the point mutations introduced into the vRNA 3' sequence, and active when being used as a single-stranded template segment, e.g. in the 'forked' structure.

For this purpose we constructed pHL1124, three complementary point mutations introduced at the 5' end of the vRNA sequence again in positions 3, 5 and 8 (U3C, GSA, A8G). Together with a sequence wild-type vRNA 3' end these variations again result in a panhandle structure free of mismatches and, therefore, pHL1124 is equivalent in this regard to pHL1104, but different in the sequence of its template and non-template single strands. No significant CAT expression was detected for pHL1124. We conclude that the increased CAT activity of pHL1104 is not a consequence of the stabilized panhandle structure itself, but at least in part is a consequence of the individual nucleotide exchanges at positions $\overline{3}$, $\overline{5}$ and $\overline{8}$ at the 3' end of the vRNA sequence, it is also more likely then to originate from other structural intermediates of initiation than a stabilized panhandle.

Mutational Analyses of Concerted Exchanges at Both Ends of the vRNA Sequence

In order to determine in detail the influence of single, double and triple exchanges at the vRNA 5' end upon CAT expression rates we also used the improved vRNA 3' end sequences of pHL1104 and pHL1102 as starting points rather than the corresponding wild-type sequence. From the series of experiments related to pHL1104 and from the equivalent series related to pHL1102 it can be concluded that retaining a G residue in position 5 is the most important single feature in these 5' end variations. A single exchange into an A residue at position 5 as in pHL1185 will render the promoter entirely inactive, while single exchanges in positions 3 or 8, as well as a 3 plus 8 double exchange will retain promoter activity even if reduced from the level observed for pHL1104, but still above wild-type expression rates. While the GSA nucleotide substitution opposite nucleotide $C\overline{5}$ in the 3' terminus results in losing one basepair (in the panhandle context) within the pHL1104 series, a basepair is indeed gained by exactly the same GSA exchange within the pHL1102 series, i.e. opposite the U5 residue as present in the pHL1102 vRNA 3' end. Since again the G5A exchange results in loss of promoter function inspire of gaining one basepair we conclude that the guanosine at position 5 may be important for RNA polymerase binding within the 5' non-template single strand rather than being part of the panhandle double-stranded structure in this region. The importance of a G residue at this position has been shown earlier in a single-step mutational analysis (Li and Palese, 1992), while non-template strand binding of RNA polymerase has been studied recently in vitro (Tiley et al., 1994). Different from the deleterious effect of an exchange at position 5 exchanges at positions 3 and in particular 8 are of minor importance.

The series of 5' nucleotide exchanges has also been repeated for the pHL1102 version of the vRNA 3' end yielding exactly the same pattern of results, albeit at the somewhat reduced levels characteristic for pHL1102. The only result in both series not quite in agreement with a uniquely important role for a G-residue in position 5 is the triple exchange of pHL1126 which retains low promoter activity in spite of an A residue in that position. Due to altogether six concerted exchanges in positions 3, 5 and 8 as well as $\overline{3}$, $\overline{5}$ and $\overline{8}$ from the 5' and 3' end of the vRNA sequence the pHL1126 vRNA panhandle structure is indeed nearly equivalent to a wild-type cRNA panhandle, with the exception of an unpaired adenosine being present in position 10 of pHL1126 while an unpaired uridine at position 10 is part of the wild-type cRNA structure. This correlation may indicate a correct structure in pHL1126 for several other residues of (minor) importance which, therefore, apparently allows to compensate for the missing G residue in position 5, even if at a clearly reduced level of activity. In the parallel pHL1102 series the corresponding triple exchange clone pHL1125 does not show any promoter activity; however, because of its deviation at position 5 it does not completely resemble the cRNA panhandle structure.

Mutational Analysis of the Panhandle Bulge Structure around Nucleotide 10

An extra, unpaired residue in position 10 at the 5' end is a specific feature of the influenza viral RNA panhandle structure. It is causing or at least enforcing a major bulge of the structure, together with unpaired residues at position 9, and might be part of a specific recognition element of that structure by viral RNA polymerase. In order to investigate the importance of that particular structural feature, a further series of plasmid constructs has been initiated, again based on pHL1104 and its 3' terminal sequence as a reference. A perfectly matched RNA double-strand without any bulge has been achieved either by inserting an additional U residue in the 3' end sequence opposite AIO (pHL1140) or by deleting the AIO residue from the 5' sequence (pHL1152). Finally, a bulge of opposite direction was created in the panhandle structure of pHL1164 with an extra U residue in position $\overline{10}$ of the 3' end, and position 10 deleted from the 5' end sequence. While the latter two constructs proved inactive in the CAT assay, pHL1140 did show some promoter activity, albeit at a reduced level. We conclude from this result that a bulge in this region may not be recognized directly by viral RNA polymerase but may serve as a flexible joint between two more rigid structural elements that are involved in immediate contact with viral polymerase. The necessary RNA bending may also, but less efficiently be achieved in an A-U-basepaired structure like pHL1140, while the other two structures would not permit such type of interaction with RNA polymerase. This interpretation has also been substantiated in a further series of variations in this region.

Serial Passaging of Influenza Virus Carrying Promoter Mutants

Figure 2:
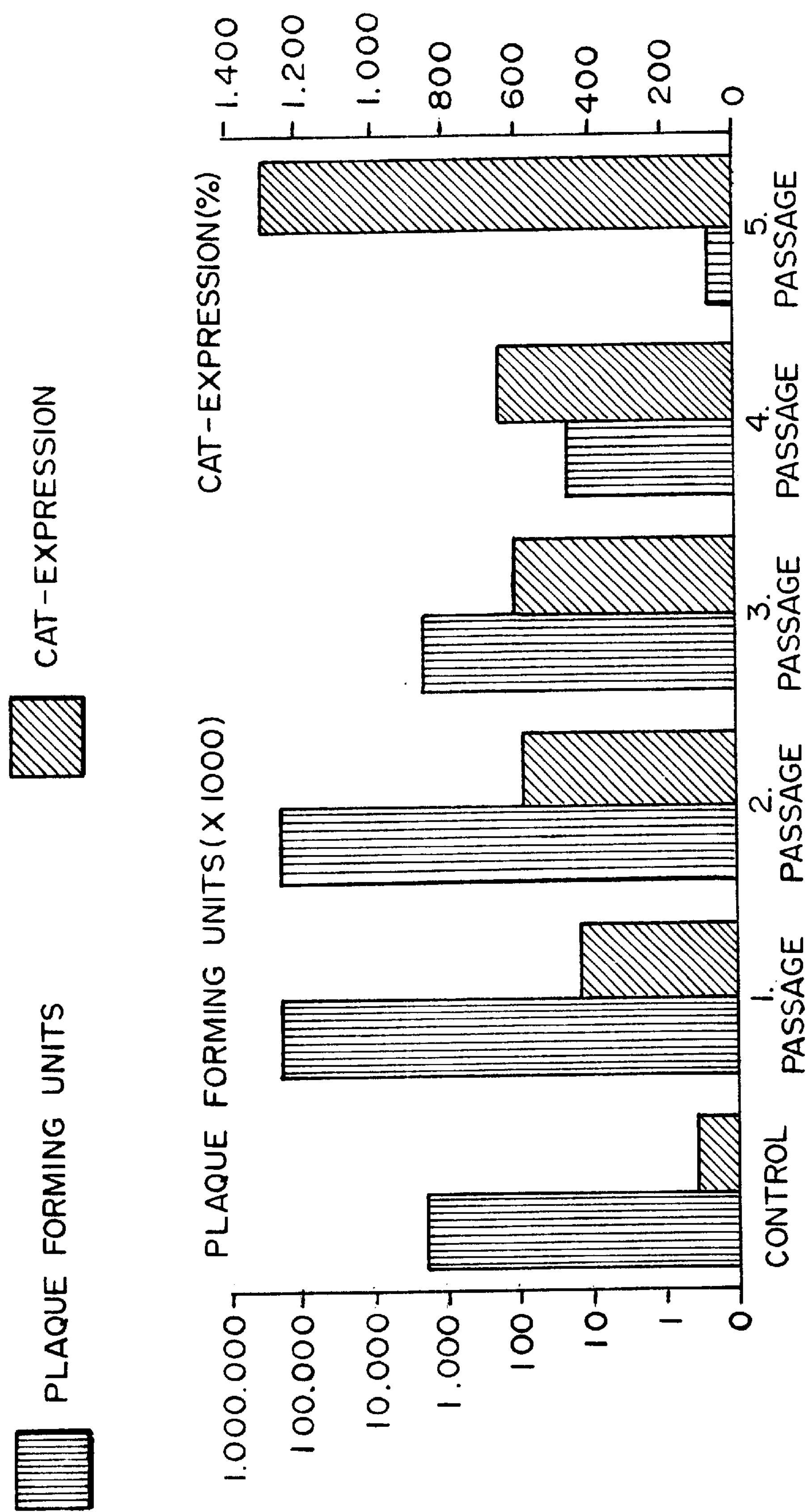

All previous experiments consisted of a first measurement of viral mRNA synthesis in DNA-transfected and infected B82 cells, followed by a second measurement of viral mRNA synthesis in infected MDCK cells, after passaging of progeny virus containing supernatants. CAT expression in infected cells upon viral passaging requires packaging of pseudo-viral vRNAs, in addition to new rounds of viral mRNA synthesis in those cells leading to CAT expression again. All viral promoter mutants analysed and found active in transfected and helper-infected B82 cells also resulted in CAT expression after transfer, and consistently in equivalent ratios of activity. Packaging, therefore, cannot be correlated with any specific element in the vRNA promoter structure so far, and does not appear to be a limiting factor in constructing influenza virus mutants in this system. While CAT expression after passaging in general appeared to be increased over the levels before passaging this might have been simply the result of different cells being used for the first and second step of CAT analysis, with MDCK being superior to B82 cells in influenza mRNA synthesis and also in progeny yields. Therefore, several experiments of serial passage have been performed using pHL1104 derived influenza supernatants and others, in MDCK cells. In these serial passages, always done using aliquots of supernatants harvested eight hours after infection for further transfer, a stepwise increase of CAT expression is observed (FIG. 2). Apparently the superior performance of viral RNA promoters carrying sequence deviations according to pHL1104 is not only true for viral mRNA synthesis, but also for viral RNA replication.

Therefore, mutant viral RNAs of this character become accumulated and effectively selected in further passaging, while packaging may be a neutral event in this regard, at least for the variants analysed here.

Serial Passaging Extended

During further passaging of supernatants the CAT containing influenza segment carrying the mutationally altered viral promotor sequences became accumulated in a stepwise manner in the population of progeny viruses. In order to demonstrate this effect on the level of individual viruses being transferred we isolated in three indepentent experiments 50 to 85 plaques each after a third round of passage on MDCK cells. Each cell lysate obtained for the individual plaques was assayed for CAT activity according to the standard protocol. While in two of the experiments the fraction of CAT positive plaques was in the range of 4 to 8% (1 out of 50, 4 out of 40 plaques) in one of these series this fraction amounted to 47% (19 of 40 plaques). Both of these results demonstrate a substantial increase over the initial fraction of CAT-segment containing virus, which may be calculated to be in the range of $10^{-5}$ or at most $10^{-4}$, and slight variations in the conditions of growth during three steps of transfer may precipitate to result in the observed differences of CAT positive plaques. While every CAT positive plaque demonstrates the amplification of nine (not eight) viral RNA segments present in the initially infected cell, this may have resulted from a single virus carrying nine or more RNA segments or from coinfection by two defective viruses able to complement each other.

Necessarily, accumulation of a pseudo-viral segment not contributiong to viral growth will, in further steps, become lethal to viral growth, even if a majority of virions may contain an average of eleven rather than eight RNA segments (Hsu et. al. 1987). Packaging of viral RNA-segments based on a general packaging signal identical for all eight segments and realized via a specific interaction chain: vRNA panhandle structure-viral RNA polymerase-viral NP protein-viral M1 protein will reflect the pools of the various vRNA segments in infected cells, and therefore may be biased towards an RNA segment superior in replication and over-represented in that pool. Biased replication and packaging will, however, lead to accumulation of lethal viral particles due to an imbalance between the eight (or nine) viral RNA segments. This prediction is borne out in continuing the viral passage of pHL1104 derived influenza supernatants beyond step three as exemplified in FIG. 2. While CAT expression based on transcription of the pHL1104 derived pseudoviral RNA segments is increased further up to the fifth passage the number of viable viruses reaches a maximum already after the second step of viral passaging, thus demonstrating the continuous accumulation of an over-replicated foreign segment, based on a superior panhandle sequence.

At a stage representing the third or fourth passage as displayed in FIG. 2 a virus preparation obtained in this way can be regarded as the equivalent of an attenuated viral strain. While the concentration of attenuated virus particles that can be achieved in this way may appear to be limited a stage equivalent to passage 4 in FIG. 2 may be delayed upon coinfection with wild-type helper virus during first or second steps of transfer, and considerably increased concentrations of attenuated virus preparations might be achievable in this way.

pHL1104-mediated high-rate expression of foreign proteins can also be used (after two or more steps of amplification via serial passaging on MDCK cells) for high rate synthesis of foreign proteins in embryonated chicken eggs, following a general method of preparation of viral stocks as used for influenza and other viruses, i.e. injection of virus suspensions into the yolk sac. Protein preparations isolated from those embryonated and infected cells will be glykosylated and modified in other ways according to their origination from eukaryotic cells.

A second method of influenza virus attenuation has been achieved via cleavage of either one of the influenza viral RNAs, preferably the M or NP gene (segments 7 or 5), via ribozyme hydrolysis in a specialized mode of action. The ribozyme RNAs which may be covalently inserted into the pSV2neo early mRNA, located between the neomycin resistance gene and the small t intron sequence originating from SV40 viral DNA, or expressed from similar expression cassettes, are directed against the 5' end sequence of segment 7 (or another of the influenza vRNA segments).

During initiation of mRNA synthesis the 5' terminal sequence which is involved in formation of the panhandle structure is at first covered by viral RNA polymerase in association with that double stranded promoter region. It will, however, become single-stranded and free of protein, since the polymerase molecule will start transcription at the 3' end and move along the 3' template sequence while synthezising a perfectly hybridizing 5' RNA daughter strand, superior in that regard to the parental panhandle 5' segment. Ribozyme RNAs which may be inhibited in their activity either by RNA substrates involved in double strand formation or if RNA substrates are covered by protein, have been directed with a 3' complementary sequence towards that protein-free 5' sequence of the substrate vRNA molecule for initiation of hybridization, which then will be extended across the entire complementary region of approximately 100 nucleotides i. e. well into the vRNA sequence initially covered by NP protein.

A second feature of the ribozyme RNAs as applied for inactivation of influenza vRNA molecules is their double-unit hammerhead character, directed against not one, but two close GUY cleavage sites, e. g. $GUU_{16}$ and $GUU_{36}$ in segment 7 or $GUC_{30}$ and $GUC_{48}$ in segment 5, which are also known to be invariable in sequence comparisons of influenza isolates.

Both features of anti-influenza ribozymes as pointed out contribute to a reduction of typically two logs (up to three logs) in production of viral progeny in template ribozyme DNA transfected cells as compared to infection of mock transfected cells, both at moi 1 and 20 h after Lipofectamnin-DNA treatment. Ribozyme treatment can be applied after two or three rounds in MDCK cells of pHL1104-promoted amplification of a pseudo-viral RNA segment originating from RNA-Polymerase I transcription, in the presence of helper virus as used in initial superinfection.

In a simple version ribozyme treatment as described above is employed as a selection technique. Here, its application is appropriate if the pseudoviral RNA is indeed a (foreign) influenza segment carrying particular mutations but capable in principle to act as a functional substitute for the helper viral segment destroyed by ribozyme cleavage. For that purpose the substitute viral segment to be selected in that procedure has to be mutagenized in advance at the two cleavage sites indicated above in order to become resistant against ribozyme interference. In another application ribozyme cleavage of helpervirus vRNA can be used for attenuation of recombinant influenza virus preparations. Here, the pseudo-viral RNA segment may be designed in a way which renders it incapable to substitute for a helpervirus gene. Therefore, viral passaging into ribozyme template DNA transfected cells would lead to an abortive infection only, because of ribozyme mediated destruction of an important viral gene, if its gene product would not be added for complementation via expression from a cDNA construct which is also DNA-transfected into the cell together with ribozyme-expressing DNA 20 h before viral infection. In this way viral progeny is obtained that is attenuated because of ribozyme cleavage of one of the vRNA segments, and effectively that segment is missing in the virions because it can no longer be packaged. Viral preparations obtained in this way are capable of only one round of infection because of their inherent M1+M2 protein complementation, and therefore are suited for vaccination purposes. Animal infection with progeny virus as isolated after the ribozyme attenuation step results in abortive infection, but viral proteins synthesized in infected cells are able to induce B-cell and T-cell responses in such animals.

In influenza viral RNA synthesis parental negative-strand vRNA is copied into plus-strand cRNA, which again is copied into progeny vRNA, from the first to the last nucleotide. This amplification of viral RNAs, however, proceeds in an inherently asymmetric way, since vRNA molecules are synthesized in excess over cRNA molecules. This result is consistent with the idea that cRNA carries a promoter structure more active in binding viral RNA polymerase and in initiation of RNA synthesis, i.e. 'stronger' than does vRNA. While at first simply the two 3' ends of single-stranded vRNA and cRNA templates have been implicated as promoter sequences, the detection of double-stranded panhandle structures involving both ends of the vRNA sequence in virions (Hsu et al., 1987) suggested more complicated substrates for RNA polymerase binding and initiation of daughter-strand synthesis. A slightly different panhandle structure has also been observed with model vRNA molecules in the absence of viral proteins in vitro (Baudin et al., 1994), possibly calling for a structural change upon viral RNA polymerase binding, i.e. a bulge may be shifted from position 4 to position 10 in that reaction (see FIG. 1). While originally several of the RNA polymerase/vRNA binding experiments in vitro appeared to show recognition only of 3' end oligonucleotides, this has since been shown to be an artifact after pure, recombinant viral polymerase free of residual RNA became available, instead of enzyme preparations from virions. Under these conditions RNA polymerase binding to viral RNA as well as endonucleolytic cleavage of cellular mRNAs by subunit PB2 was observed to depend on vRNA 5' plus 3' terminal sequence binding, with even higher affinity for the 5' non-template segment (Hagen et al., 1994; Tiley et al., 1994).

Different from the employment of both vRNA and cRNA promoter structures in replication physiologically only vRNA promoters will also serve in initiation of viral mRNA synthesis according to the cap-snatching mechanism (Plotch et al., 1979; Braam et al., 1983). While it has been claimed that cRNA promoters would not have the capacity to act according to this scheme (Tiley et al., 1994), the failure to observe viral antisense mRNA molecules may simply reflect the inavailability of cRNA molecules early in infection, i.e. in the absence of surplus viral NP protein, and small amounts of such molecules might even have gone undetected. In this invention we describe a mutagenizational analysis of the vRNA promoter structure in vivo which in approaching the structure of the cRNA promoter via three nucleotide exchanges shows considerably improved activity in viral mRNA synthesis over vRNA promoter wild-type levels. Continuing increase of viral CAT mRNA expression during consecutive steps of. viral passaging suggests that the same vRNA promoter mutants also show increased activity in cRNA synthesis, both in accordance with the idea that the cRNA promoter structure might be 'stronger' than the vRNA promoter, also in initiation of viral mRNA synthesis.

Additional variations of the 5' terminal sequence clearly indicate the major importance of a G residue in position 5, irrespective of complementarity or not to position 5 at the 3' end. The unique role of this G residue has been observed before in a serial mutagenizational analysis (Li and Palese, 1992). According to both data guanosine residue 5 may be involved in single-strand binding of RNA polymerase as has indeed been observed for the non-template strand terminal segment (Tiley et al., 1994). While panhandle double-strand structures are likely to constitute the initial RNA polymerase binding substrate a partial separation of template and non-template strands is expected to take place consecutively resulting in a 'forked structure' such as proposed by Fodor et al. (1994). Specific and tight binding of RNA polymerase in this structure may predominantly be oriented towards sequence elements in the non-template strand, since the growing point of RNA synthesis will have to move along the entire template strand following its initiation. It is, therefore, possible that such a binding interaction survives most or all of an individual round of mRNA synthesis as has been proposed (Tiley et al., 1994).

The triple nucleotide exchanges as introduced in vRNA molecules derived from pHL1104 templates will create three additional basepairs able to stabilize the panhandle structure in general, but more specifically they will favor a bulged adenosine 10 over the bulged adenosine 4 conformation as observed for the wild-type sequence in vitro (Baudin et al., 1994). Since the changes introduced here lead to a considerable enhancement of promoter activity we propose that a bulged conformation may be the structure underlying the vRNA/polymerase binding reaction, which otherwise would have to be achieved only as a result of that interaction. A bulged 10 adenosine residue may constitute a kind of flexible joint or angular kink which in turn suggests two major, structurally stable binding sites to the left and right of this element. One of these sites has to be the double-stranded sequence element of (in average) six basepairs extending from positions 11 to 16 and $\overline{10}$to $\overline{15}$, respectively. While the distal three basepairs are known to be variable for the various RNA segments, basepair 13/$\overline{12}$has been shown to be exchangeable experimentally, and also the number of basepairs has been reduced to four without complete loss of function (Luo et al., 1991). With all of these data it seems clear that the main recognition element in this region is an RNA double-strand of certain stability, while it remains possible that residue 12 guanosine and potentially others are also recognized individually within that structure. A major second binding element for RNA polymerase on the other side relative to position is less evident, but may be located in a distance of nearly one helical turn in the de-bulged region around position 4, since direct contacts are suggested by that initial conformational interaction, and also by the specific requirement of a guanosine residue in position 5, which is likely to interact not only during, but also before partial strand separation in that region, i.e. in the panhandle as well as the forked structure. While an extra adenosine residue in position 10 may be optimal for creating a correctly shaped bulge in this region of RNA, structural variants are possible in this regard (see pHL1140) which excludes direct interactions between RNA polymerase and residues constituting that bulge.

In summary we are proposing a model (see FIG. 1) of consecutive steps of interaction between a vRNA or cRNA promoter structure and viral RNA polymerase:

bulged 4 panhandle→bulged 10 panhandle/polymerase→forked RNA/polymerase (bound to 5G and ds element 11-16)→initiation of RNA synthesis (recognition of 3' end of template).

Attenuation of influenza viruses for preparation of a live nasal vaccine relies on two mechanisms: 1) preferential amplification of a recombinant viral segment carrying the pHL1104 promoter mutation, which will increase its rate in packaged viral RNP particles and indirectly decrease that of the eight helper virus RNP particles. This competition results in an increase of defective viruses from which one or more of the regular viral gene segments are missing. 2) Sequence specific ribozyme cleavage of one or more helper virus RNA segments, if compensated through gene product expression for. functional complementation. This dual interaction will result in virus progeny, which is capable of only one round of infection, abortive because of the missing viral protein(s) that are required for their propagation. —Ribozyme cleavage of one out of two sister viral gene segments, sensitive and (artificially) insensitive for its hydrolysis may also be used (repeatedly) for selection purposes, including selection for viral gene constructs expressed via RNA polymerase I transcription.

Materials and Methods

Plasmid Constructions

Plasmids with mutated vRNA and/or mutated cRNA promoter sequences are derivatives of pHL926 (Zobel et al., 1993; Neumann et al., 1994). In pHL926 a hybrid CAT cDNA with flanking non-coding sequences derived from influenza vRNA segments has been precisely inserted in antisense orientation between mouse rDNA promoter and terminator sequences. The CAT reporter gene in this way has been introduced by exactly replacing the coding sequence for hemagglutinin, retaining the untranslated viral 5' and 3' sequences of segment 4.

vRNA 5' end mutations were created by PCR, using a general primer hybridizing to a position in the flanking rDNA promoter sequence, and a specific primer carrying the desired nucleotide substitution to be introduced in the viral terminal sequence. The polymerase chain reaction products were first digested by the restriction enzymes Bg/II and SpeI, inserted into the left boundary position by exchanging the segment between these appropriate restricton sites in pHL926, and finally confirmed in their constitution by DNA Sanger sequencing.

Generation of vRNA 3' end mutations followed the same general scheme at the right boundary. PCR products were obtained by using a general primer complementary to a CAT gene internal sequence position, and a specific primer with appropriate nucleotide exchanges inserted into its sequence. Following digestion with restriction enzymes NcoI and ScaI, the PCR products were cloned into NcoI- and ScaI (partially)-digested plasmid pHL926. Any PCR derived sequences were investigated by DNA sequencing.

For constructs with both 5' end and 3' end mutations in combination, 5' variation containing fragments were obtained by Bg/II and SpeI restriction and inserted into the appropriate 3' terminal variation plasmids.

Cells and Viruses

Influenza A/FPV/Bratislava viruses were grown in NIH3T3 cells. For transfection and passaging experiments B82 cells (a mouse L cell line) and MDCK cells were used.

Lipofectamin DNA Transfection and Influenza Virus Helper Infection

For DNA transfection $10^7$ B82 cells were used. 5 $\mu$g of plasmid DNA were mixed with 60 $\mu$g of Lipofectarnin (Lipofectamin™, GIBCO/BRL) in serum-free medium and incubated at room temperature for 10–15 min. This mixture was added to the cells washed twice with serum-free medium, and the incubation with Lipofectamin/DNA was continued for 1 hr. After further incubation with DMEM medium for 1 hr the transfected B82 cells were infected with influenza A/FPV/Bratislava at a multiplicity of infection of 0.01 to 1 for another 30–60 min. Further incubation was performed with DMEM medium.

Passaging of Virus Containing Supernatants

Under standard conditions 8 hr after influenza infection (at moi 0.1 to 1) cells were harvested for CAT assays, and supernatants were collected and spun down at 1200 rpm for 5 min for removal of cell debris.

Aliquots of virus containing cleared supernatants were used for plaque tests, and another aliquot was adsorbed to $10^7$ MDCK cells for 30–60 min for further passaging. Again 8 hr after infection the CPE was verified, and cells and supernatants were collected and treated as before.

CAT Assay

Cell extracts were prepared as described by Gorman et al. (1982). CAT assays were done with [$^{14}$C]chloramphenicol or fluorescent-labeled chloramphenicol (borondipyrromethane difluoride fluorophore; FLASH CAT Kit, Stratagene) as substrates.

For [$^{14}$C]chloramphenicol the assay mixture contained: 0.1 $\mu$Ci [$^{14}$C]chloramphenicol, 20 $\mu$l 4 mM Acetyl-CoA, 25 $\mu$l I M Tris-HCl (pH 7.5) and 50 $\mu$l of cell lysate in a total volume of 150 $\mu$l. The assay mixture for the fluorescent-labeled substrate contained (in a final volume of 80 $\mu$l): 10 $\mu$l 0.25 M Tris-HCl (pH 7.5), 10 $\mu$l 4 M Acetyl-CoA, 10 $\mu$l fluorescent-labeled chloramphenicol, and 50 $\mu$l of cell lysate. After an incubation time of 16 hr the reaction products were separated by chromatography and either autoradiographed or visualized by UV illumination and photography.

References

Baudin, F., Bach, C., Cusack, S. and Ruigrok, R. W. H. (1994) The *EMBO J*., 13, 3158–3165.

Braam, J., Uhmanen, I. and Krug, R. (1983) *Cell*, 34, 609–618.

Compans, R. W., Content, J. and Duesberg, P. H. (1972) *J. Virol*., 10, 795–800.

Fodor, E., Seong, B. L. and Brownlee, G. G. (1993) *J. Gen. Virol*., 74, 1327–1333.

Fodor, E., Pritlove, D. C. and Brownlee, G. G. (1994) *J. Virol*., 68, 4092–4096.

Gorman, M., Moffat, L. and Howard, B. (1982) *Mol. Cell Biol*., 2, 1044–1057.

Hagen, M., Chung, T. D. Y., Butcher, J. A. and Krystal, M. (1994) *J. Virol*., 68, 1509–1515.

Honda, A., Ueda, K., Nagata, K. and Ishihama, A. (1987) *J. Biochem*., 102, 1241–1249.

Hsu, M., Parvin, J. D., Gupta, S., Krystal, M. and Palese, P. (1987) *Proc. Natl. Acad. Sci. USA*, 84, 8140–8144.

Li, X and Palese, P. (1992) *J. Virol*., 66, 4331–4338.

Luo, G., Luytjes, W., Enami, M. and Palese, P. (1991) *J. Virol*., 65, 2861–2867.

Martin, J., Albo, C., Ortin, J., Melero, J. A. and Portela, A. (1992) *J. Gen. Virol*., 73, 1855–1859.

Neumann, G., Zobel, A. and Hobom, G. (1994) *Virology*, 202, 477–479.

Plotch, S., Bouloy, M. and Krug, R. M. (1979) *Proc. Natl. Acad Sci. USA*, 76, 1618–1622.

Seong, B. L. and Brownlee, G. G. (1992) *J. Virol*., 73, 3115–3124.

Shapiro, G. and Krug, R. (1988) *J. Virol*., 62, 2285–2290.

Tiley, L. S., Hagen, M., Matthews, J. T. and Krystal, M. (1994) *J. Virol*., 68, 5108–5116.

Yamanaka, K., Ogasawara, N., Yoshikawa, H., Ishihama, A. and Nagata, K. (1991) *Proc. Natl. Acad. Sci. USA*, 88: 5369–5373.

Zobel, A., Neumann, G. and Hobom, G. (1993) *Nucl. Acids Res*., 21, 3607–3614.

Legends to Figures

Figure 1B:
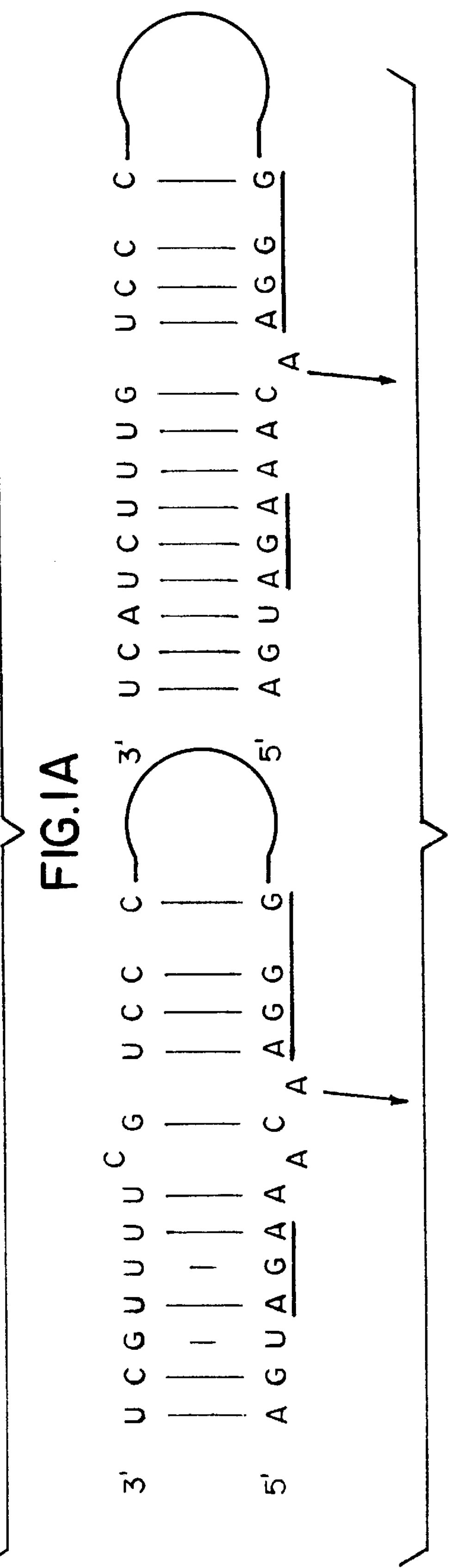

FIG. 1. Proposed scheme of consecutive conformational steps occurring prior to initiation of viral mRNA synthesis in influenza vRNA, in wild-type and pHL1104 derived mutant sequences. Positions of triple mutation in pHL1104 vRNA are indicated in bold and larger size letters.

(A) Free RNA panhandle structure, bulged at position 4 (wild-type vRNA; Baudin et al, 1994) or at position 10 (mutant vRNA). (B) Bulged 10 panhandle structures after binding of viral RNA polymerase; proposed protein binding positions marked by underlignments. (C) Forked structures of partial strand separation. (D) Initiation of viral mRNA synthesis via hybridization of capped primer oligonucleotide.

FIG. 2. Serial passaging of pHL1104-derived progeny viruses.

$10^7$ B82 cells were transfected with 5$\mu$ of pHL1104 DNA (in 60 $\mu$g Lipofectamin) and infected two hours later with influenza A/FPV/Bratislava (m.o.i:1). 8 hr post-infection the cells were assayed for plaque forming units (dark column) and for CAT activity (hatched column) After sedimentation an other aliquot of the supernatant was adsorbed to $10^7$ MDCK cells. Further rounds of passaging were done equivalently by harvesting the cells 8 hr after infection for assaying CAT activities, whereas an aliquot of the supernatant was always adsorbed to fresh MDCK cells. Numbers of serial passages are indicated at the bottom. Plaque forming units per ml refer to the left ordinate, CAT expression rates (relative to primary infection levels) to the ordinate on the right.

What is claimed is:

1. An influenza virus comprising at least one segment comprising a vRNA nucleotide sequence comprising a 3' terminal nucleotide sequence and a 5' terminal nucleotide sequence in association therewith, wherein said 3' terminal nucleotide sequence consists of 15 nucleotides corresponding to a wild-type influenza virus vRNA 3' terminal nucleotide sequence modified by replacement of the three nucleotides naturally occurring in the wild-type 3' terminal nucleotide sequence at positions $\overline{3}$, $\overline{5}$ and $\overline{8}$ by other nucleotides, and wherein said influenza virus exhibits as a result of said replacements a rate of transcription, replication or expression that is higher than that of a wild-type influenza virus of the same species as measured in a cell infected with said virus through transcription of vRNA by cellular RNA polymerase I and secondary transcription of said vRNA as a template into viral mRNA by viral polymerase.

2. An influenza virus according to claim 1, wherein the replacements in the 3' terminal nucleotide sequence comprise G$\overline{3}$A and C$\overline{8}$U.

3. An influenza virus according to claim 2, wherein the replacements in the 3' terminal nucleotide sequence consist of G$\overline{3}$A, C$\overline{8}$U and U$\overline{5}$C.

4. An influenza virus according to claim 3, which comprises a 3' terminal nucleotide sequence of 5'-CCUGUUUCUACU-3' (SEQ. ID No:9).

5. An influenza virus according to claim 1, which further comprises a nucleotide sequence encoding at least one non-viral gene.

6. An influenza virus according to claim 1, wherein said at least one segment is a segment which does not occur naturally in a wild-type influenza of the same species.

7. An influenza virus according to claim 6, wherein said segment which does not occur naturally in a wild-type influenza virus of the same species comprises a nucleotide sequence which encodes a protein or peptide which is not expressed by said wild-type influenza virus of the same species.

8. An influenza virus according to claim 7, wherein said protein or peptide which is not expressed by said wild-type influenza virus of the same species is a protein or peptide selected from the group consisting of antigens and T-cell epitopes.

9. An influenza virus according to claim 8, which comprises multiple copies of said nucleotide sequence which encodes said protein or peptide.

10. An influenza virus according to claim 8, wherein the antigen or T-cell epitope is from a virus selected from the group consisting of human immunodeficiency virus, herpes virus, rhinovirus, CMV, papilloma viruses, hepatitis viruses and hog cholera virus.

11. An influenza virus according to any one of claims 1–10, which further comprises a 5' terminal nucleotide sequence consisting of a corresponding wild-type influenza virus vRNA 5' terminal nucleotide sequence modified by replacement of the nucleotides naturally occurring in the wild-type 5' terminal nucleotide sequence at positions 3 and 8 by other nucleotides.

12. An antigenic composition comprising an influenza virus according to any one of claims 1–10.

13. An antigenic composition comprising an influenza virus according to claim 11.

* * * * *

UNITED STATES PATENT AND TRADEMARK OFFICE

CERTIFICATE OF CORRECTION

PATENT NO. : 6,524,588 B1
APPLICATION NO. : 08/809513
DATED : February 25, 2003
INVENTOR(S) : Hobom et al.

It is certified that error appears in the above-identified patent and that said Letters Patent is hereby corrected as shown below:

Column 41, Line 32, "influenza of" should read -- influenza virus of --

Signed and Sealed this

Twenty-second Day of May, 2007

JON W. DUDAS
*Director of the United States Patent and Trademark Office*

SEQUENCE LISTING

```
(1) GENERAL INFORMATION:

   (iii) NUMBER OF SEQUENCES: 9


(2) INFORMATION FOR SEQ ID NO: 1:

     (i) SEQUENCE CHARACTERISTICS:
          (A) LENGTH:   5241 base pairs
          (B) TYPE:   nucleic acid
          (C) STRANDEDNESS: double
```

-continued (D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Influenza virus, RNA sequence
(B) INDIVIDUAL ISOLATE: pHL926

(xi) SEQUENCE DESCRIPTION: SEQ ID NO: 1:

```
CTGGCGGCAG TAGCGCGGTG GTCCCACCTG ACCCCATGCC GAACTCAGAA GTGAAACGCC     60
GTAGCGCCGA TGGTAGTGTG GGGTCTCCCC ATGCGAGAGT AGGGAACTGC CAGGCATCAA    120
ATAAAACGAA AGGCTCAGTC GAAAGACTGG GCCTTTCGTT TTATCTGTTG TTTGTCGGTG    180
AACGCTCTCC TGAGTAGGAC AAATCCGCCG GGAGCGGATT TGAACGTTGC GAAGCAACGG    240
CCCGGAGGGT GGCGGGCAGG ACGCCCGCCA TAAACTGCCA GGCATCAAAT TAAGCAGAAG    300
GCCATCCTGA CGGATGGCCT TTTTGCGTTT CTACAAACTC TTTTGTTTAT TTTTCTAAAT    360
ACATTCAAAT ATGTATCCGC TCATGAGACA ATAACCCTGA TAAATGCTTC AATAATATTG    420
AAAAAGGAAG AGTATGAGTA TTCAACATTT CCGTGTCGCC CTTATTCCCT TTTTTGCGGC    480
ATTTTGCCTT CCTGTTTTTG CTCACCCAGA AACGCTGGTG AAAGTAAAAG ATGCTGAAGA    540
TCAGTTGGGT GCACGAGTGG GTTACATCGA ACTGGATCTC AACAGCGGTA AGATCCTTGA    600
GAGTTTTCGC CCCGAAGAAC GTTTTCCAAT GATGAGCACT TTTAAAGTTC TGCTATGTGG    660
CGCGGTATTA TCCCGTGTTG ACGCCGGGCA AGAGCAACTC GGTCGCCGCA TACACTATTC    720
TCAGAATGAC TTGGTTGAGT ACTCACCAGT CACAGAAAAG CATCTTACGG ATGGCATGAC    780
AGTAAGAGAA TTATGCAGTG CTGCCATAAC CATGAGTGAT AACACTGCGG CCAACTTACT    840
TCTGACAACG ATCGGAGGAC CGAAGGAGCT AACCGCTTTT TTGCACAACA TGGGGGATCA    900
TGTAACTCGC CTTGATCGTT GGGAACCGGA GCTGAATGAA GCCATACCAA ACGACGAGCG    960
TGACACCACG ATGCCTGCAG CAATGGCAAC AACGTTGCGC AAACTATTAA CTGGCGAACT   1020
ACTTACTCTA GCTTCCCGGC AACAATTAAT AGACTGGATG GAGGCGGATA AAGTTGCAGG   1080
ACCACTTCTG CGCTCGGCCC TTCCGGCTGG CTGGTTTATT GCTGATAAAT CTGGAGCCGG   1140
TGAGCGTGGG TCTCGCGGTA TCATTGCAGC ACTGGGGCCA GATGGTAAGC CCTCCCGTAT   1200
CGTAGTTATC TACACGACGG GGAGTCAGGC AACTATGGAT GAACGAAATA GACAGATCGC   1260
TGAGATAGGT GCCTCACTGA TTAAGCATTG GTAACTGTCA GACCAAGTTT ACTCATATAT   1320
ACTTTAGATT GATTTAAAAC TTCATTTTTA ATTTAAAAGG ATCTAGGTGA AGATCCTTTT   1380
TGATAATCTC ATGACCAAAA TCCCTTAACG TGAGTTTTCG TTCCACTGAG CGTCAGACCC   1440
CGTAGAAAAG ATCAAAGGAT CTTCTTGAGA TCCTTTTTTT CTGCGCGTAA TCTGCTGCTT   1500
GCAAACAAAA AAACCACCGC TACCAGCGGT GGTTTGTTTG CCGGATCAAG AGCTACCAAC   1560
TCTTTTTCCG AAGGTAACTG GCTTCAGCAG AGCGCAGATA CCAAATACTG TCCTTCTAGT   1620
GTAGCCGTAG TTAGGCCACC ACTTCAAGAA CTCTGTAGCA CCGCCTACAT ACCTCGCTCT   1680
GCTAATCCTG TTACCAGTGG CTGCTGCCAG TGGCGATAAG TCGTGTCTTA CCGGGTTGGA   1740
CTCAAGACGA TAGTTACCGG ATAAGGCGCA GCGGTCGGGC TGAACGGGGG GTTCGTGCAC   1800
ACAGCCCAGC TTGGAGCGAA CGACCTACAC CGAACTGAGA TACCTACAGC GTGAGCATTG   1860
AGAAAGCGCC ACGCTTCCCG AAGGGAGAAA GGCGGACAGG TATCCGGTAA GCGGCAGGGT   1920
CGGAACAGGA GAGCGCACGA GGGAGCTTCC AGGGGGAAAC GCCTGGTATC TTTATAGTCC   1980
```

-continued

```
TGTCGGGTTT CGCCACCTCT GACTTGAGCG TCGATTTTTG TGATGCTCGT CAGGGGGGCG   2040
GAGCCTATGG AAAAACGCCA GCAACGCGGC CCGAGATGCG CCGCGTGCGG CTGCTGGAGA   2100
TGGCGGACGC GATGGATATG TTCTGCCAAG GGTTGGTTTG CGCATTCACA GTTCTCCGCA   2160
AGAATTGATT GGCTCCAATT CTTGGAGTGG TGAATCCGTT AGCGAGGTGC CGCCGGCTTC   2220
CATTCAGGTC GAGGTGGCCC GGCTCCATGC ACCGCGACGC AACGCGGGGA GGCAGACAAG   2280
GTATAGGGCG GCGCCTACAA TCCATGCCAA CCCGTTCCAT GTGCTCGCCG AGGCGGCATA   2340
AATCGCCGTG ACGATCAGCG GTCCAGTGAT CGAAGTTAGG CTGGTAAGAG CCGCGAGCGA   2400
TCCTTGAAGC TGTCCCTGAT GGTCGTCATC TACCTGCCTG GACAGCATGG CCTGCAACGC   2460
GGGCATCCCG ATGCCGCCGG AAGCGAGAAG AATCATAATG GGGAAGGCCA TCCAGCCTCG   2520
CGTCGCGAAC GCCAGCAAGA CGTAGCCCAG CGCGTCGGCC AGCTTGCAAT TCGCGCTAAC   2580
TTACATTAAT TGCGTTGCGC TCACTGCCCG CTTTCCAGTC GGGAAACCTG TCGTGCCAGC   2640
TGCATTAATG AATCGGCCAA CGCGCGGGGA GAGGCGGTTT GCGTATTGGG CGCCAGGGTG   2700
GTTTTTCTTT TCACCAGTGA GACGGGCAAC AGCTGATTGC CCTTCACCGC CTGGCCCTGA   2760
GAGAGTTGCA GCAAGCGGTC CACGCTGGTT TGCCCCAGCA GGCGAAAATC CTGTTTGATG   2820
GTGGTTGACG GCGGGATATA ACATGAGCTG TCTTCGGTAT CGTCGTATCC CACTACCGAG   2880
ATATCCGCAC CAACGCGCAG CCCGGACTCG GTAATGGCGC GCATTGCGCC CAGCGCCATC   2940
TGATCGTTGG CAACCAGCAT CGCAGTGGGA ACGATGCCCT CATTCAGCAT TTGCATGGTT   3000
TGTTGAAAAC CGGACATGGC ACTCCAGTCG CCTTCCCGTT CCGCTATCGG CTGAATTTGA   3060
TTGCGAGTGA GATATTTATG CCAGCCAGCC AGACGCAGAC GCGCCGAGAC AGAACTTAAT   3120
GGGCCCCCGG TGACAGGGAC AGAGAGGGCT TCTGGAGGAA AAAAGAAAAA AAAAAAAAAA   3180
GATCCAAAGC TCCAGGGCGA GCTCGAATTC CCCGGTAAAG CCGCTTAAGA CATTCCCGCT   3240
CTTACACATC CCAGCCCTGA AAAAGGGCAT CAAAATAAAC CACACCTATG GTGTATGCAT   3300
TTACGTTGAC ACCATCGAAT GGTGCAAAAC CTTTCGCGGT ATGGCATGAT AGCGCCCGGA   3360
AGAGAGTCAA TTCAGGGTGG TGAATGTGAA ACCAGTAACG TTATACGATG TCGCAGAGTA   3420
TGCCGGTGTC TCTTATCAGA CCGTTTCCCG CGTGGTGAAC CAGGCCAGCC ACGTTTCTGC   3480
GAAAACGCGG GAAAAAGTGG AAGCGGCGAT GGCGGAGCTG AATTACATTC CCAACCGCGT   3540
GGCACAACAA CTGGCGGGCA AACAGTCGTT GCTGATTGGC GTTGCCACCT CCAGTCTGGC   3600
CCTGCACGCG CCGTCGCAAA TTGTCGCGGC GATTAAATCT CGCGCCGATC AACTGGGTGC   3660
CAGCGTGGTG GTGTCGATGG TAGAACGAAG CGGCGTCGAA GCCTGTAAAG CGGCGGTGCA   3720
CAATCTTCTC GCGCAACGCG TTCAGTGGGC TAGATCTACC GCGGTAGATC ATTAACTATC   3780
CGCTGGATGA CCAGGATGCC ATTGCTGTGG AAGCTGCCTG CACTAATGTT CCGGCGTTAT   3840
TTCTTGATGT CTCTGACCAG ACACCCATCA ACAGTATTAT TTTCTCCCAT GAAGACGGTA   3900
CGCGACTGGG CGTGGAGCAT CTGGTCGCAT TGGGTCACCA GCAAATCGCG CTGTTAGCGG   3960
GCCCTGTACG TCTGAGGCCG AGGGAAAGCT ATGGGCGCGG TTTTCTTTCA TTGACCTGTC   4020
GGTCTTATCA GTTCTCCGGG TTGTCAGGTC GACCAGTTGT TCCTTTGAGG TCCGGTTCTT   4080
TTCGTTATGG GGTCATTTTT GGGCCACCTC CCCAGGTATG ACTTCCAGGT ATTCTCTGTG   4140
GCCTGTCACT TTCCTCCCTG TCTCTTTTAT GCTTGTGATC TTTTAGATCT GGTCCTATTG   4200
GACCTGGAGA TAGGTAGTAG AAACAAGGGT GTTTTTAAAT ACTAGTACAT TACGCCCCGC   4260
CCTGCCACTC ATCGCAGTAC TGTTGTAATT CATTAAGCAT TCTGCCGACA TGGAAGCCAT   4320
```

-continued

```
CACAGACGGC ATGATGAACC TGAATCGCCA GCGGCATCAG CACCTTGTCG CCTTGCGTAT   4380

AATATTTGCC CATGGTGAAA ACGGGGGCGA AGAAGTTGTC CATATTGGCC ACGTTTAAAT   4440

CAAAACTGGT GAAACTCACC CAGGGATTGG CTGAGACGAA AAACATATTC TCAATAAACC   4500

CTTTAGGGAA ATAGGCCAGG TTTTCACCGT AACACGCCAC ATCTTGCGAA TATATGTGTA   4560

GAAACTGCCG GAAATCGTCG TGGTATTCAC TCCAGAGCGA TGAAAACGTT TCAGTTTGCT   4620

CATGGAAAAC GGTGTAACAA GGGTGAACAC TATCCCATAT CACCAGCTCA CCGTCTTTCA   4680

TTGCCATACG GAATTCCGGA TGAGCATTCA TCAGGCGGGC AAGAATGTGA ATAAAGGCCG   4740

GATAAAACTT GTGCTTATTT TTCTTTACGG TCTTTAAAAA GGCCGTAATA TCCAGCTGAA   4800

CGGTCTGGTT ATAGGTACAT TGAGCAACTG ACTGAAATGC CTCAAAATGT TCTTTACGAT   4860

GCCATTGGGA TATATCAACG GTGGTATATC CAGTGATTTT TTTCTCCATG ATTAATAGAA   4920

TTATCCCCTG TTTCTACTCC CCCCCAACTT CGGAGGTCGA CCAGTACTCC GGGCGAAACT   4980

TTGTTTTTTT TTTTTCCCCC GATGCTGGAG GTCGACCAGA TGTCCGAAAG TGTCCCCCCC   5040

CCCCCCCCCC CCCGGCGCGG AACGGCGGGG CCACTCTGGA CTCTTTTTTT TTTTTTTTTT   5100

TTTTTTTTTG GGGATCCTCT AGAGTCGACC TGCAGCCCAA GCTAGCGGCC GCTAGCTTCT   5160

GTTTTGGCGG ATGAGAGAAG ATTTTCAGCC TGATACAGAT TAAATCAGAA CGCAGAAGCG   5220

GTCTGATAAA ACAGAATTTG C                                             5241
```

(2) INFORMATION FOR SEQ ID NO: 2:

(i) SEQUENCE CHARACTERISTICS:
(A) LENGTH: 5241 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Influenza virus, RNA sequence
(C) INDIVIDUAL ISOLATE: pHL1104

(xi) SEQUENCE DESCRIPTION: SEQ ID NO: 2:

```
CTGGCGGCAG TAGCGCGGTG GTCCCACCTG ACCCCATGCC GAACTCAGAA GTGAAACGCC     60

GTAGCGCCGA TGGTAGTGTG GGGTCTCCCC ATGCGAGAGT AGGGAACTGC CAGGCATCAA    120

ATAAAACGAA AGGCTCAGTC GAAAGACTGG GCCTTTCGTT TTATCTGTTG TTTGTCGGTG    180

AACGCTCTCC TGAGTAGGAC AAATCCGCCG GGAGCGGATT TGAACGTTGC GAAGCAACGG    240

CCCGGAGGGT GGCGGGCAGG ACGCCCGCCA TAAACTGCCA GGCATCAAAT TAAGCAGAAG    300

GCCATCCTGA CGGATGGCCT TTTTGCGTTT CTACAAACTC TTTTGTTTAT TTTTCTAAAT    360

ACATTCAAAT ATGTATCCGC TCATGAGACA ATAACCCTGA TAAATGCTTC AATAATATTG    420

AAAAAGGAAG AGTATGAGTA TTCAACATTT CCGTGTCGCC CTTATTCCCT TTTTTGCGGC    480

ATTTTGCCTT CCTGTTTTTG CTCACCCAGA AACGCTGGTG AAAGTAAAAG ATGCTGAAGA    540

TCAGTTGGGT GCACGAGTGG GTTACATCGA ACTGGATCTC AACAGCGGTA AGATCCTTGA    600

GAGTTTTCGC CCCGAAGAAC GTTTTCCAAT GATGAGCACT TTTAAAGTTC TGCTATGTGG    660

CGCGGTATTA TCCCGTGTTG ACGCCGGGCA AGAGCAACTC GGTCGCCGCA TACACTATTC    720

TCAGAATGAC TTGGTTGAGT ACTCACCAGT CACAGAAAAG CATCTTACGG ATGGCATGAC    780
```

-continued

```
AGTAAGAGAA TTATGCAGTG CTGCCATAAC CATGAGTGAT AACACTGCGG CCAACTTACT    840
TCTGACAACG ATCGGAGGAC CGAAGGAGCT AACCGCTTTT TTGCACAACA TGGGGGATCA    900
TGTAACTCGC CTTGATCGTT GGGAACCGGA GCTGAATGAA GCCATACCAA ACGACGAGCG    960
TGACACCACG ATGCCTTCAG CAATGGCAAC AACGTTGCGC AAACTATTAA CTGGCGAACT   1020
ACTTACTCTA GCTTCCCGGC AACAATTAAT AGACTGGATG GAGGCGGATA AAGTTGCAGG   1080
ACCACTTCTG CGCTCGGCCC TTCCGGCTGG CTGGTTTATT GCTGATAAAT CTGGAGCCGG   1140
TGAGCGTGGG TCTCGCGGTA TCATTGCAGC ACTGGGGCCA GATGGTAAGC CCTCCCGTAT   1200
CGTAGTTATC TACACGACGG GGAGTCAGGC AACTATGGAT GAACGAAATA GACAGATCGC   1260
TGAGATAGGT GCCTCACTGA TTAAGCATTG GTAACTGTCA GACCAAGTTT ACTCATATAT   1320
ACTTTAGATT GATTTAAAAC TTCATTTTTA ATTTAAAAGG ATCTAGGTGA AGATCCTTTT   1380
TGATAATCTC ATGACCAAAA TCCCTTAACG TGAGTTTTCG TTCCACTGAG CGTCAGACCC   1440
CGTAGAAAAG ATCAAAGGAT CTTCTTGAGA TCCTTTTTTT CTGCGCGTAA TCTGCTGCTT   1500
GCAAACAAAA AAACCACCGC TACCAGCGGT GGTTTGTTTG CCGGATCAAG AGCTACCAAC   1560
TCTTTTTCCG AAGGTAACTG GCTTCAGCAG AGCGCAGATA CCAAATACTG TCCTTCTAGT   1620
GTAGCCGTAG TTAGGCCACC ACTTCAAGAA CTCTGTAGCA CCGCCTACAT ACCTCGCTCT   1680
GCTAATCCTG TTACCAGTGG CTGCTGCCAG TGGCGATAAG TCGTGTCTTA CCGGGTTGGA   1740
CTCAAGACGA TAGTTACCGG ATAAGGCGCA GCGGTCGGGC TGAACGGGGG GTTCGTGCAC   1800
ACAGCCCAGC TTGGAGCGAA CGACCTACAC CGAACTGAGA TACCTACAGC GTGAGCATTG   1860
AGAAAGCGCC ACGCTTCCCG AAGGGAGAAA GGCGGACAGG TATCCGGTAA GCGGCAGGGT   1920
CGGAACAGGA GAGCGCACGA GGGAGCTTCC AGGGGGAAAC GCCTGGTATC TTTATAGTCC   1980
TGTCGGGTTT CGCCACCTCT GACTTGAGCG TCGATTTTTG TGATGCTCGT CAGGGGGGCG   2040
GAGCCTATGG AAAAACGCCA GCAACGCGGC CCGAGATGCG CCGCGTGCGG CTGCTGGAGA   2100
TGGCGGACGC GATGGATATG TTCTGCCAAG GGTTGGTTTG CGCATTCACA GTTCTCCGCA   2160
AGAATTGATT GGCTCCAATT CTTGGAGTGG TGAATCCGTT AGCGAGGTGC CGCCGGCTTC   2220
CATTCAGGTC GAGGTGGCCC GGCTCCATGC ACCGCGACGC AACGCGGGGA GGCAGACAAG   2280
GTATAGGGCG GCGCCTACAA TCCATGCCAA CCCGTTCCAT GTGCTCGCCG AGGCGGCATA   2340
AATCGCCGTG ACGATCAGCG GTCCAGTGAT CGAAGTTAGG CTGGTAAGAG CCGCGAGCGA   2400
TCCTTGAAGC TGTCCCTGAT GGTCGTCATC TACCTGCCTG GACAGCATGG CCTGCAACGC   2460
GGGCATCCCG ATGCCGCCGG AAGCGAGAAG AATCATAATG GGGAAGGCCA TCCAGCCTCG   2520
CGTCGCGAAC GCCAGCAAGA CGTAGCCCAG CGCGTCGGCC AGCTTGCAAT TCGCGCTAAC   2580
TTACATTAAT TGCGTTGCGC TCACTGCCCG CTTTCCAGTC GGGAAACCTG TCGTGCCAGC   2640
TGCATTAATG AATCGGCCAA CGCGCGGGGA GAGGCGGTTT GCGTATTGGG CGCCAGGGTG   2700
GTTTTTCTTT TCACCAGTGA GACGGGCAAC AGCTGATTGC CCTTCACCGC CTGGCCCTGA   2760
GAGAGTTGCA GCAAGCGGTC CACGCTGGTT TGCCCCAGCA GGCGAAAATC CTGTTTGATG   2820
GTGGTTGACG GCGGGATATA ACATGAGCTG TCTTCGGTAT CGTCGTATCC CACTACCGAG   2880
ATATCCGCAC CAACGCGCAG CCCGGACTCG GTAATGGCGC GCATTGCGCC CAGCGCCATC   2940
TGATCGTTGG CAACCAGCAT CGCAGTGGGA ACGATGCCCT CATTCAGCAT TTGCATGGTT   3000
TGTTGAAAAC CGGACATGGC ACTCCAGTCG CCTTCCCGTT CCGCTATCGG CTGAATTTGA   3060
TTGCGAGTGA GATATTTATG CCAGCCAGCC AGACGCAGAC GCGCCGAGAC AGAACTTAAT   3120
GGGCCCCCGG TGACAGGGAC AGAGAGGGCT TCTGGAGGAA AAAAGAAAAA AAAAAAAAAA   3180
```

-continued

```
GATCCAAAGC TCCAGGGCGA GCTCGAATTC CCCGGTAAAG CCGCTTAAGA CATTCCCGCT   3240

CTTACACATC CCAGCCCTGA AAAAGGGCAT CAAAATAAAC CACACCTATG GTGTATGCAT   3300

TTACGTTGAC ACCATCGAAT GGTGCAAAAC CTTTCGCGGT ATGGCATGAT AGCGCCCGGA   3360

AGAGAGTCAA TTCAGGGTGG TGAATGTGAA ACCAGTAACG TTATACGATG TCGCAGAGTA   3420

TGCCGGTGTC TCTTATCAGA CCGTTTCCCG CGTGGTGAAC CAGGCCAGCC ACGTTTCTGC   3480

GAAAACGCGG GAAAAAGTGG AAGCGGCGAT GGCGGAGCTG AATTACATTC CCAACCGCGT   3540

GGCACAACAA CTGGCGGGCA AACAGTCGTT GCTGATTGGC GTTGCCACCT CCAGTCTGGC   3600

CCTGCACGCG CCGTCGCAAA TTGTCGCGGC GATTAAATCT CGCGCCGATC AACTGGGTGC   3660

CAGCGTGGTG GTGTCGATGG TAGAACGAAG CGGCGTCGAA GCCTGTAAAG CGGCGGTGCA   3720

CAATCTTCTC GCGCAACGCG TTCAGTGGGC TAGATCTACC GCGGTAGATC ATTAACTATC   3780

CGCTGGATGA CCAGGATGCC ATTGCTGTGG AAGCTGCCTG CACTAATGTT CCGGCGTTAT   3840

TTCTTGATGT CTCTGACCAG ACACCCATCA ACAGTATTAT TTTCTCCCAT GAAGACGGTA   3900

CGCGACTGGG CGTGGAGCAT CTGGTCGCAT TGGGTCACCA GCAAATCGCG CTGTTAGCGG   3960

GCCCTGTACG TCTGAGGCCG AGGGAAAGCT ATGGGCGCGG TTTTCTTTCA TTGACCTGTC   4020

GGTCTTATCA GTTCTCCGGG TTGTCAGGTC GACCAGTTGT TCCTTTGAGG TCCGGTTCTT   4080

TTCGTTATGG GGTCATTTTT GGGCCACCTC CCCAGGTATG ACTTCCAGGT ATTCTCTGTG   4140

GCCTGTCACT TTCCTCCCTG TCTCTTTTAT GCTTGTGATC TTTTAGATCT GGTCCTATTG   4200

GACCTGGAGA TAGGTAGTAG AAACAAGGGT GTTTTTAAAT ACTAGTACAT TACGCCCCGC   4260

CCTGCCACTC ATCGCAGTAC TGTTGTAATT CATTAAGCAT TCTGCCGACA TGGAAGCCAT   4320

CACAGACGGC ATGATGAACC TGAATCGCCA GCGGCATCAG CACCTTGTCG CCTTGCGTAT   4380

AATATTTGCC CATGGTGAAA ACGGGGGCGA AGAAGTTGTC CATATTGGCC ACGTTTAAAT   4440

CAAAACTGGT GAAACTCACC CAGGGATTGG CTGAGACGAA AAACATATTC TCAATAAACC   4500

CTTTAGGGAA ATAGGCCAGG TTTTCACCGT AACACGCCAC ATCTTGCGAA TATATGTGTA   4560

GAAACTGCCG GAAATCGTCG TGGTATTCAC TCCAGAGCGA TGAAAACGTT TCAGTTTGCT   4620

CATGGAAAAC GGTGTAACAA GGGTGAACAC TATCCCATAT CACCAGCTCA CCGTCTTTCA   4680

TTGCCATACG GAATTCCGGA TGAGCATTCA TCAGGCGGGC AAGAATGTGA ATAAAGGCCG   4740

GATAAAACTT GTGCTTATTT TTCTTTACGG TCTTTAAAAA GGCCGTAATA TCCAGCTGAA   4800

CGGTCTGGTT ATAGGTACAT TGAGCAACTG ACTGAAATGC CTCAAAATGT TCTTTACGAT   4860

GCCATTGGGA TATATCAACG GTGGTATATC CAGTGATTTT TTTCTCCATG ATTAATAGAA   4920

TTATCCCCTG TTTCTACTCC CCCCCAACTT CGGAGGTCGA CCAGTACTCC GGGCGAAACT   4980

TTGTTTTTTT TTTTTCCCCC GATGCTGGAG GTCGACCAGA TGTCCGAAAG TGTCCCCCCC   5040

CCCCCCCCCC CCCGGCGCGG AACGGCGGGG CCACTCTGGA CTCTTTTTTT TTTTTTTTTT   5100

TTTTTTTTTG GGGATCCTCT AGAGTCGACC TGCAGCCCAA GCTAGCGGCC GCTAGCTTCT   5160

GTTTTGGCGG ATGAGAGAAG ATTTTCAGCC TGATACAGAT TAAATCAGAA CGCAGAAGCG   5220

GTCTGATAAA ACAGAATTTG C                                             5241
```

(2) INFORMATION FOR SEQ ID NO: 3:

(i) SEQUENCE CHARACTERISTICS:
- (A) LENGTH: 13 base pairs
- (B) TYPE: nucleic acid
- (C) STRANDEDNESS: single
- (D) TOPOLOGY: linear (ii) MOLECULE TYPE: RNA (genomic)

(iii) HYPOTHETICAL: NO (iv) ANTI-SENSE: NO (iv) ANTI-SENSE: NO (vi) ORIGINAL SOURCE:
(A) ORGANISM: Influenza virus, 3' RNA sequence
(B) INDIVIDUAL ISOLATE: Wild Type vRNA Promoter Element (xi) SEQUENCE DESCRIPTION: SEQ ID NO: 3:

CCCUGCUUUU GCU 13

(2) INFORMATION FOR SEQ ID NO: 4:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (iv) ANTI-SENSE: NO (vi) ORIGINAL SOURCE:
(A) ORGANISM: Influenza virus, vRNA 3' sequence
(B) INDIVIDUAL ISOLATE: pHL1104 vRNA Promoter Element (xi) SEQUENCE DESCRIPTION: SEQ ID NO: 4:

CCCUGUUUCU ACU 13

(2) INFORMATION FOR SEQ ID NO: 5:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (iv) ANTI-SENSE: NO (vi) ORIGINAL SOURCE:
(A) ORGANISM: Influenza virus, vRNA 5' sequence
(C) INDIVIDUAL ISOLATE: vRNA Promoter element (xi) SEQUENCE DESCRIPTION: SEQ ID NO: 5:

AGUAGAAACA AGGG 14

(2) INFORMATION FOR SEQ ID NO: 6:

(i) SEQUENCE CHARACTERISTICS:
(A) LENGTH: 6802 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:

-continued (A) ORGANISM: Influenza virus, RNA sequence
(C) INDIVIDUAL ISOLATE: pHL1191

(xi) SEQUENCE DESCRIPTION: SEQ ID NO: 6:

```
CTAGACTCTT CAAGCAAAAG CAGGTAGATC TTGAAAGATG AGTCTTCTAA CCGAGGTCGA     60
AACGTACGTT CTCTCTATCA TCCCGTCAGG CCCCCTCAAA GCCGAGATCG CACAGAGACT    120
TGAAGATGTC TTTGCAGGGA AGAACACCGA TCTTGAGGTT CTCATGGAAT GGCTAAAGAC    180
AAGACCAATC CTGTCACCTC TGACTAAGGG GATTTTAGGA TTTGTGTTCA CGCTCACCGT    240
GCCCAGTGAG CGAGGACTGC AGCGTAGACG CTTTGTCCAA AATGCCCTTA ATGGGAACGG    300
GGATCCAAAT AACATGGACA AAGCAGTTAA ACTGTATAGG AAGCTCAAGA GGGAGATAAC    360
ATTCCATGGG GCCAAAGAAA TCTCACTCAG TTATTCTGCT GGTGCACTTG CCAGTTGTAT    420
GGGCCTCATA TACAACAGGA TGGGGGCTGT GACCACTGAA GTGGCATTTG GCCTGGTATG    480
TGCAACCTGT GAACAGATTG CTGACTCCCA GCATCGGTCT CATAGGCAAA TGGTGACAAC    540
AACCAACCCA CTAATCAGAC ATGAGAACAG AATGGTTTTA GCCAGCACTA CAGCTAAGGC    600
TATGGAGCAA ATGGCTGGAT CGAGTGAGCA AGCAGCAGAG GCCATGGAGG TTGCTAGTCA    660
GGCTAGGCAA ATGGTGCAAG CGATGAGAAC CATTGGGACT CATCCTAGCT CCAGTGCTGG    720
TCTGAAAAAT GCTCTTCTTG AAAATTTGCA GGCCTATCAG AAACGAATGG GGGTGCAGAT    780
GCAACGGTTC AAGTGATCCT CTCGCTATTG CCGCAAATAT CATTGGGATC TTGCACTTGA    840
TATTGTGGAT TCTTGATCGT CTTTTTTTCA AATGCATTTA CCGTCGCTTT AAATACGGAC    900
TGAAAGGAGG GCCTTCTACG GAAGGAGTGC CAAAGTCTAT GAGGGAAGAA TATCGAAAGG    960
AACAGCAGAG TGCTGTGGAT GCTGACGATG GTCATTTTGT CAGCATAGAG CTGGAGTAAA   1020
AAACTACCAT ATGGGGCATG TCCCAAGTAT GTTAAGCAAA ACACTCTGAA GTTGGCAACA   1080
GGGATGCGGA ATGTACCAGA GAAACAAACT AGAGGCATAT TCGGCGCAAT AGCAGGTTTC   1140
ATAGAAAATG GTTGGGAGGG AATGATAGAC GGTTGGTACG GTTTCAGGCA TCAAAATTCC   1200
GAGGGCACAG GACAAGCAGC AGATCTTAAA AGCACTCAAG CAGCCATCGA CCAAATCAAT   1260
GGGAAACTGA ATAGGGTAAT CGAGAAGACG AACGAGAAAT TCCATCAAAT CGAAAAGGAA   1320
TTCTCAGAAG TAGAAGGGAG AATTCAGGAC CTCGAGCATG CATCTAGAGG GCCCTATTCT   1380
ATAGTGTCAC CTAAATGCTA GAGCTCGCTG ATCAGCCTCG ACTGTGCCTT CTAGTTGCCA   1440
GCCATCTGTT GTTTGCCCCT CCCCCGTGCC TTCCTTGACC CTGGAAGGTG CCACTCCCAC   1500
TGTCCTTTCC TAATAAAATG AGGAAATTGC ATCGCATTGT CTGAGTAGGT GTCATTCTAT   1560
TCTGGGGGGT GGGGTGGGGC AGGACAGCAA GGGGGAGGAT TGGGAAGACA ATAGCAGGCA   1620
TGCTGGGGAT GCGGTGGGCT CTATGGCTTC TGAGGCGGAA AGAACCAGCT GGGGCTCTAG   1680
GGGGTATCCC CACGCGCCCT GTAGCGGCGC ATTAAGCGCG GCGGGTGTGG TGGTTACGCG   1740
CAGCGTGACC GCTACACTTG CCAGCGCCCT AGCGCCCGCT CCTTTCGCTT TCTTCCCTTC   1800
CTTTCTCGCC ACGTTCGCCG GCTTTCCCCG TCAAGCTCTA AATCGGGGCA TCCCTTTAGG   1860
GTTCCGATTT AGTGCTTTAC GGCACCTCGA CCCCAAAAAA CTTGATTAGG GTGATGGTTC   1920
ACGTAGTGGG CCATCGCCCT GATAGACGGT TTTTCGCCCT TTGACGTTGG AGTCCACGTT   1980
CTTTAATAGT GGACTCTTGT TCCAAACTGG AACAACACTC AACCCTATCT CGGTCTTATT   2040
CTTTTGATTT ATAAGGGATT TGGGGATTTC GGCCTATTGG TTAAAAAATG AGCTGATTTA   2100
ACAAAAATTT AACGCGAATT AATTCTGTGG AATGTGTGTC AGTTAGGGTG TGGAAAGTCC   2160
CCAGGCTCCC CAGGCAGGCA GAAGTATGCA AAGCATGCAT CTCAATTAGT CAGCAACCAG   2220
```

-continued

```
GTGTGGAAAG TCCCCAGGCT CCCCAGCAGG CAGAAGTATG CAAAGCATGC ATCTCAATTA   2280

GTCAGCAACC ATAGTCCCGC CCCTAACTCC GCCCATCCCG CCCCTAACTC CGCCCAGTTC   2340

CGCCCATTCT CCGCCCCATG GCTGACTAAT TTTTTTTATT TATGCAGAGG CCGAGGCCGC   2400

CTCTGCCTCT GAGCTATTCC AGAAGTAGTG AGGAGGCTTT TTTGGAGGCC TAGGCTTTTG   2460

CAAAAAGCTC CCGGGAGCTT GTATATCCAT TTTCGGATCT GATCAAGAGA CAGGATGAGG   2520

ATCGTTTCGC ATGATTGAAC AAGATGGATT GCACGCAGGT TCTCCGGCCG CTTGGGTGGA   2580

GAGGCTATTC GGCTATGACT GGGCACAACA GACAATCGGC TGCTCTGATG CCGCCGTGTT   2640

CCGGCTGTCA GCGCAGGGGC GCCCGGTTCT TTTTGTCAAG ACCGACCTGT CCGGTGCCCT   2700

GAATGAACTG CAGGACGAGG CAGCGCGGCT ATCGTGGCTG GCCACGACGG GCGTTCCTTG   2760

CGCAGCTGTG CTCGACGTTG TCACTGAAGC GGGAAGGGAC TGGCTGCTAT TGGGCGAAGT   2820

GCCGGGGCAG GATCTCCTGT CATCTCACCT TGCTCCTGCC GAGAAAGTAT CCATCATGGC   2880

TGATGCAATG CGGCGGCTGC ATACGCTTGA TCCGGCTACC TGCCCATTCG ACCACCAAGC   2940

GAAACATCGC ATCGAGCGAG CACGTACTCG GATGGAAGCC GGTCTTGTCG ATCAGGATGA   3000

TCTGGACGAA GAGCATCAGG GGCTCGCGCC AGCCGAACTG TTCGCCAGGC TCAAGGCGCG   3060

CATGCCCGAC GGCGAGGATC TCGTCGTGAC CCATGGCGAT GCCTGCTTGC CGAATATCAT   3120

GGTGGAAAAT GGCCGCTTTT CTGGATTCAT CGACTGTGGC CGGCTGGGTG TGGCGGACCG   3180

CTATCAGGAC ATAGCGTTGG CTACCCGTGA TATTGCTGAA GAGCTTGGCG GCGAATGGGC   3240

TGACCGCTTC CTCGTGCTTT ACGGTATCGC CGCTCCCGAT TCGCAGCGCA TCGCCTTCTA   3300

TCGCCTTCTT GACGAGTTCT TCTGAGCGGG ACTCTGGGGT TCGAAATGAC CGACCAAGCG   3360

ACGCCCAACC TGCCATCACG AGATTTCGAT TCCACCGCCG CCTTCTATGA AAGGTTGGGC   3420

TTCGGAATCG TTTTCCGGGA CGCCGGCTGG ATGATCCTCC AGCGCGGGGA TCTCATGCTG   3480

GAGTTCTTCG CCCACCCCAA CTTGTTTATT GCAGCTTATA ATGGTTACAA ATAAAGCAAT   3540

AGCATCACAA ATTTCACAAA TAAAGCATTT TTTTCACTGC ATTCTAGTTG TGGTTTGTCC   3600

AAACTCATCA ATGTATCTTA TCATGTCTGT ATACCGTCGA CCTCTAGCTA GAGCTTGGCG   3660

TAATCATGGT CATAGCTGTT TCCTGTGTGA AATTGTTATC CGCTCACAAT TCCACACAAC   3720

ATACGAGCCG GAAGCATAAA GTGTAAAGCC TGGGGTGCCT AATGAGTGAG CTAACTCACA   3780

TTAATTGCGT TGCGCTCACT GCCCGCTTTC CAGTCGGGAA ACCTGTCGTG CCAGCTGCAT   3840

TAATGAATCG GCCAACGCGC GGGGAGAGGC GGTTTGCGTA TTGGGCGCTC TTCCGCTTCC   3900

TCGCTCACTG ACTCGCTGCG CTCGGTCGTT CGGCTGCGGC GAGCGGTATC AGCTCACTCA   3960

AAGGCGGTAA TACGGTTATC CACAGAATCA GGGGATAACG CAGGAAAGAA CATGTGAGCA   4020

AAAGGCCAGC AAAAGGCCAG GAACCGTAAA AAGGCCGCGT TGCTGGCGTT TTTCCATAGG   4080

CTCCGCCCCC CTGACGAGCA TCACAAAAAT CGACGCTCAA GTCAGAGGTG GCGAAACCCG   4140

ACAGGACTAT AAAGATACCA GGCGTTTCCC CCTGGAAGCT CCCTCGTGCG CTCTCCTGTT   4200

CCGACCCTGC CGCTTACCGG ATACCTGTCC GCCTTTCTCC CTTCGGGAAG CGTGGCGCTT   4260

TCTCAATGCT CACGCTGTAG GTATCTCAGT TCGGTGTAGG TCGTTCGCTC CAAGCTGGGC   4320

TGTGTGCACG AACCCCCCGT TCAGCCCGAC CGCTGCGCCT TATCCGGTAA CTATCGTCTT   4380

GAGTCCAACC CGGTAAGACA CGACTTATCG CCACTGGCAG CAGCCACTGG TAACAGGATT   4440

AGCAGAGCGA GGTATGTAGG CGGTGCTACA GAGTTCTTGA AGTGGTGGCC TAACTACGGC   4500

TACACTAGAA GGACAGTATT TGGTATCTGC GCTCTGCTGA AGCCAGTTAC CTTCGGAAAA   4560

AGAGTTGGTA GCTCTTGATC CGGCAAACAA ACCACCGCTG GTAGCGGTGG TTTTTTTGTT   4620
```

-continued

```
TGCAAGCAGC AGATTACGCG CAGAAAAAAA GGATCTCAAG AAGATCCTTT GATCTTTTCT   4680

ACGGGGTCTG ACGCTCAGTG GAACGAAAAC TCACGTTAAG GGATTTTGGT CATGAGATTA   4740

TCAAAAAGGA TCTTCACCTA GATCCTTTTA AATTAAAAAT GAAGTTTTAA ATCAATCTAA   4800

AGTATATATG AGTAAACTTG GTCTGACAGT TACCAATGCT TAATCAGTGA GGCACCTATC   4860

TCAGCGATCT GTCTATTTCG TTCATCCATA GTTGCCTGAC TCCCCGTCGT GTAGATAACT   4920

ACGATACGGG AGGGCTTACC ATCTGGCCCC AGTGCTGCAA TGATACCGCG AGACCCACGC   4980

TCACCGGCTC CAGATTTATC AGCAATAAAC CAGCCAGCCG GAAGGGCCGA GCGCAGAAGT   5040

GGTCCTGCAA CTTTATCCGC CTCCATCCAG TCTATTAATT GTTGCCGGGA AGCTAGAGTA   5100

AGTAGTTCGC CAGTTAATAG TTTGCGCAAC GTTGTTGCCA TTGCTACAGG CATCGTGGTG   5160

TCACGCTCGT CGTTTGGTAT GGCTTCATTC AGCTCCGGTT CCCAACGATC AAGGCGAGTT   5220

ACATGATCCC CCATGTTGTG CAAAAAAGCG GTTAGCTCCT TCGGTCCTCC GATCGTTGTC   5280

AGAAGTAAGT TGGCCGCAGT GTTATCACTC ATGGTTATGG CAGCACTGCA TAATTCTCTT   5340

ACTGTCATGC CATCCGTAAG ATGCTTTTCT GTGACTGGTG AGTACTCAAC CAAGTCATTC   5400

TGAGAATAGT GTATGCGGCG ACCGAGTTGC TCTTGCCCGG CGTCAATACG GGATAATACC   5460

GCGCCACATA GCAGAACTTT AAAAGTGCTC ATCATTGGAA AACGTTCTTC GGGGCGAAAA   5520

CTCTCAAGGA TCTTACCGCT GTTGAGATCC AGTTCGATGT AACCCACTCG TGCACCCAAC   5580

TGATCTTCAG CATCTTTTAC TTTCACCAGC GTTTCTGGGT GAGCAAAAAC AGGAAGGCAA   5640

AATGCCGCAA AAAAGGGAAT AAGGGCGACA CGGAAATGTT GAATACTCAT ACTCTTCCTT   5700

TTTCAATATT ATTGAAGCAT TTATCAGGGT TATTGTCTCA TGAGCGGATA CATATTTGAA   5760

TGTATTTAGA AAAATAAACA AATAGGGGTT CCGCGCACAT TTCCCCGAAA AGTGCCACCT   5820

GACGTCGACG GATCGGGAGA TCTCCCGATC CCCTATGGTC GACTCTCAGT ACAATCTGCT   5880

CTGATGCCGC ATAGTTAAGC CAGTATCTGC TCCCTGCTTG TGTGTTGGAG GTCGCTGAGT   5940

AGTGCGCGAG CAAAATTTAA GCTACAACAA GGCAAGGCTT GACCGACAAT TGCATGAAGA   6000

ATCTGCTTAG GGTTAGGCGT TTTGCGCTGC TTCGCGATGT ACGGGCCAGA TATACGCGTT   6060

GACATTGATT ATTGACTAGT TATTAATAGT AATCAATTAC GGGGTCATTA GTTCATAGCC   6120

CATATATGGA GTTCCGCGTT ACATAACTTA CGGTAAATGG CCCGCCTGGC TGACCGCCCA   6180

ACGACCCCCG CCCATTGACG TCAATAATGA CGTATGTTCC CATAGTAACG CCAATAGGGA   6240

CTTTCCATTG ACGTCAATGG GTGGACTATT TACGGTAAAC TGCCCACTTG GCAGTACATC   6300

AAGTGTATCA TATGCCAAGT ACGCCCCCTA TTGACGTCAA TGACGGTAAA TGGCCCGCCT   6360

GGCATTATGC CCAGTACATG ACCTTATGGG ACTTTCCTAC TTGGCAGTAC ATCTACGTAT   6420

TAGTCATCGC TATTACCATG GTGATGCGGT TTTGGCAGTA CATCAATGGG CGTGGATAGC   6480

GGTTTGACTC ACGGGGATTT CCAAGTCTCC ACCCCATTGA CGTCAATGGG AGTTTGTTTT   6540

GGCACCAAAA TCAACGGGAC TTTCCAAAAT GTCGTAACAA CTCCGCCCCA TTGACGCAAA   6600

TGGGCGGTAG GCGTGTACGG TGGGAGGTCT ATATAAGCAG AGCTCTCTGG CTAACTAGAG   6660

AACCCACTGC TTACTGGCTT ATCGAAATTA ATACGACTCA CTATAGGGAG ACCCAAGCTT   6720

GGTACCGAGC TCGGATCCAC TAGTAACGGC CGCCAGTGTG CTGGAATTCT GCAGATTCTT   6780

CTCTCATCCG CCAAAACAGA AG                                            6802
```

(2) INFORMATION FOR SEQ ID NO: 7:

(i) SEQUENCE CHARACTERISTICS:

-continued (A) LENGTH: 5825 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Influenza virus, RNA sequence
(C) INDIVIDUAL ISOLATE: pHL1489

(xi) SEQUENCE DESCRIPTION: SEQ ID NO: 7:

```
CGATGGTCAT TTTGTCCTGA TGAGTCCGTG AGGACGAAAC ATAGAGCTGG AGTAAAACTG     60

ATGAGTCCGT GAGGACGAAA CTACCTTGTT TCTATTCGAA ATGACCGACC AAGCGACGCC    120

CAACCTGCCA TCACGAGATT TCGATTCCAC CGCCGCCTTC TATGAAAGGT TGGGCTTCGG    180

AATCGTTTTC CGGGACGCCG GCTGGATGAT CCTCCAGCGC GGGGATCTCA TGCTGGAGTT    240

CTTCGCCCAC CCCGGGCTCG ATCCCCTCGC GAGTTGGTTC AGCTGCTGCC TGAGGCTGGA    300

CGACCTCGCG GAGTTCTACC GGCAGTGCAA ATCCGTCGGC ATCCAGGAAA CCAGCAGCGG    360

CTATCCGCGC ATCCATGCCC CCGAACTGCA GGAGTGGGGA GGCACGATGG CCGCTTTGGT    420

CCCGGATCTT TGTGAAGGAA CCTTACTTCT GTGGTGTGAC ATAATTGGAC AAACTACCTA    480

CAGAGATTTA AAGCTCTAAG GTAAATATAA AATTTTTAAG TGTATAATGT GTTAAACTAC    540

TGATTCTAAT TGTTTGTGTA TTTTAGATTC CAACCTATGG AACTGATGAA TGGGAGCAGT    600

GGTGGAATGC CTTTAATGAG GAAAACCTGT TTTGCTCAGA AGAAATGCCA TCTAGTGATG    660

ATGAGGCTAC TGCTGACTCT CAACATTCTA CTCCTCCAAA AAGAAGAAGA AAGGTAGAAG    720

ACCCCAAGGA CTTTCCTTCA GAATTGCTAA GTTTTTTGAG TCATGCTGTG TTTAGTAATA    780

GAACTCTTGC TTGCTTTGCT ATTTACACCA CAAAGGAAAA AGCTGCACTG CTATACAAGA    840

AAATTATGGA AAAATATTCT GTAACCTTTA TAAGTAGGCA TAACAGTTAT AATCATAACA    900

TACTGTTTTT TCTTACTCCA CACAGGCATA GAGTGTCTGC TATTAATAAC TATGCTCAAA    960

AATTGTGTAC CTTTAGCTTT TTAATTTGTA AAGGGGTTAA TAAGGAATAT TTGATGTATA   1020

GTGCCTTGAC TAGAGATCAT AATCAGCCAT ACCACATTTG TAGAGGTTTT ACTTGCTTTA   1080

AAAAACCTCC CACACCTCCC CCTGAACCTG AAACATAAAA TGAATGCAAT TGTTGTTGTT   1140

AACTTGTTTA TTGCAGCTTA TAATGGTTAC AAATAAAGCA ATAGCATCAC AAATTTCACA   1200

AATAAAGCAT TTTTTTCACT GCATTCTAGT TGTGGTTTGT CCAAACTCAT CAATGTATCT   1260

TATCATGTCT GGATCCCCAG GAAGCTCCTC TGTGTCCTCA TAAACCCTAA CCTCCTCTAC   1320

TTGAGAGGAC ATTCCAATCA TAGGCTGCCC ATCCACCCTC TGTGTCCTCC TGTTAATTAG   1380

GTCACTTAAC AAAAAGGAAA TTGGGTAGGG GTTTTTCACA GACCGCTTTC TAAGGGTAAT   1440

TTTAAAATAT CTGGGAAGTC CCTTCCACTG CTGTGTTCCA GAAGTGTTGG TAAACAGCCC   1500

ACAAATGTCA ACAGCAGAAA CATACAAGCT GTCAGCTTTG CACAAGGGCC CAACACCCTG   1560

CTCATCAAGA AGCACTGTGG TTGCTGTGTT AGTAATGTGC AAAACAGGAG GCACATTTTC   1620

CCCACCTGTG TAGGTTCCAA AATATCTAGT GTTTTCATTT TTACTTGGAT CAGGAACCCA   1680

GCACTCCACT GGATAAGCAT TATCCTTATC CAAAACAGCC TTGTGGTCAG TGTTCATCTG   1740

CTGACTGTCA ACTGTAGCAT TTTTTGGGGT TACAGTTTGA GCAGGATATT TGGTCCTGTA   1800

GTTTGCTAAC ACACCCTGCA GCTCCAAAGG TTCCCCACCA ACAGCAAAAA AATGAAAATT   1860
```

-continued

```
TGACCCTTGA ATGGGTTTTC CAGCACCATT TTCATGAGTT TTTTGTGTCC CTGAATGCAA   1920
GTTTAACATA GCAGTTACCC CAATAACCTC AGTTTTAACA GTAACAGCTT CCCACATCAA   1980
AATATTTCCA CAGGTTAAGT CCTCATTTAA ATTAGGCAAA GGAATTCTTG AAGACGAAAG   2040
GGCCTCGTGA TACGCCTATT TTTATAGGTT AATGTCATGA TAATAATGGT TTCTTAGACG   2100
TCAGGTGGCA CTTTTCGGGG AAATGTGCGC GGAACCCCTA TTTGTTTATT TTTCTAAATA   2160
CATTCAAATA TGTATCCGCT CATGAGACAA TAACCCTGAT AAATGCTTCA ATAATATTGA   2220
AAAAGGAAGA GTATGAGTAT TCAACATTTC CGTGTCGCCC TTATTCCCTT TTTTGCGGCA   2280
TTTTGCCTTC CTGTTTTTGC TCACCCAGAA ACGCTGGTGA AAGTAAAAGA TGCTGAAGAT   2340
CAGTTGGGTG CACGAGTGGG TTACATCGAA CTGGATCTCA ACAGCGGTAA GATCCTTGAG   2400
AGTTTTCGCC CCGAAGAACG TTTTCCAATG ATGAGCACTT TTAAAGTTCT GCTATGTGGC   2460
GCGGTATTAT CCCGTGTTGA CGCCGGGCAA GAGCAACTCG GTCGCCGCAT ACACTATTCT   2520
CAGAATGACT TGGTTGAGTA CTCACCAGTC ACAGAAAAGC ATCTTACGGA TGGCATGACA   2580
GTAAGAGAAT TATGCAGTGC TGCCATAACC ATGAGTGATA ACACTGCGGC CAACTTACTT   2640
CTGACAACGA TCGGAGGACC GAAGGAGCTA ACCGCTTTTT TGCACAACAT GGGGGATCAT   2700
GTAACTCGCC TTGATCGTTG GGAACCGGAG CTGAATGAAG CCATACCAAA CGACGAGCGT   2760
GACACCACGA TGCCTGCAGC AATGGCAACA ACGTTGCGCA AACTATTAAC TGGCGAACTA   2820
CTTACTCTAG CTTCCCGGCA ACAATTAATA GACTGGATGG AGGCGGATAA AGTTGCAGGA   2880
CCACTTCTGC GCTCGGCCCT TCCGGCTGGC TGGTTTATTG CTGATAAATC TGGAGCCGGT   2940
GAGCGTGGGT CTCGCGGTAT CATTGCAGCA CTGGGGCCAG ATGGTAAGCC CTCCCGTATC   3000
GTAGTTATCT ACACGACGGG GAGTCAGGCA ACTATGGATG AACGAAATAG ACAGATCGCT   3060
GAGATAGGTG CCTCACTGAT TAAGCATTGG TAACTGTCAG ACCAAGTTTA CTCATATATA   3120
CTTTAGATTG ATTTAAAACT TCATTTTTAA TTTAAAAGGA TCTAGGTGAA GATCCTTTTT   3180
GATAATCTCA TGACCAAAAT CCCTTAACGT GAGTTTTCGT TCCACTGAGC GTCAGACCCC   3240
GTAGAAAAGA TCAAAGGATC TTCTTGAGAT CCTTTTTTTC TGCGCGTAAT CTGCTGCTTG   3300
CAAACAAAAA AACCACCGCT ACCAGCGGTG GTTTGTTTGC CGGATCAAGA GCTACCAACT   3360
CTTTTTCCGA AGGTAACTGG CTTCAGCAGA GCGCAGATAC CAAATACTGT CCTTCTAGTG   3420
TAGCCGTAGT TAGGCCACCA CTTCAAGAAC TCTGTAGCAC CGCCTACATA CCTCGCTCTG   3480
CTAATCCTGT TACCAGTGGC TGCTGCCAGT GGCGATAAGT CGTGTCTTAC CGGGTTGGAC   3540
TCAAGACGAT AGTTACCGGA TAAGGCGCAG CGGTCGGGCT GAACGGGGGG TTCGTGCACA   3600
CAGCCCAGCT TGGAGCGAAC GACCTACACC GAACTGAGAT ACCTACAGCG TGAGCTATGA   3660
GAAAGCGCCA CGCTTCCCGA AGGGAGAAAG GCGGACAGGT ATCCGGTAAG CGGCAGGGTC   3720
GGAACAGGAG AGCGCACGAG GGAGCTTCCA GGGGGAAACG CCTGGTATCT TTATAGTCCT   3780
GTCGGGTTTC GCCACCTCTG ACTTGAGCGT CGATTTTTGT GATGCTCGTC AGGGGGGCGG   3840
AGCCTATGGA AAAACGCCAG CAACGCGGCC TTTTTACGGT TCCTGGCCTT TTGCTGGCCT   3900
TTTGCTCACA TGTTCTTTCC TGCGTTATCC CCTGATTCTG TGGATAACCG TATTACCGCC   3960
TTTGAGTGAG CTGATACCGC TCGCCGCAGC CGAACGACCG AGCGCAGCGA GTCAGTGAGC   4020
GAGGAAGCGG AAGAGCGCCT GATGCGGTAT TTTCTCCTTA CGCATCTGTG CGGTATTTCA   4080
CACCGCATAT GGTGCACTCT CAGTACAATC TGCTCTGATG CCGCATAGTT AAGCCAGTAT   4140
ACACTCCGCT ATCGCTACGT GACTGGGTCA TGGCTGCGCC CCGACACCCG CCAACACCCG   4200
CTGACGCGCC CTGACGGGCT TGTCTGCTCC CGGCATCCGC TTACAGACAA GCTGTGACCG   4260
```

-continued

```
TCTCCGGGAG CTGCATGTGT CAGAGGTTTT CACCGTCATC ACCGAAACGC GCGAGGCAGC   4320

TGTGGAATGT GTGTCAGTTA GGGTGTGGAA AGTCCCCAGG CTCCCCAGCA GGCAGAAGTA   4380

TGCAAAGCAT GCATCTCAAT TAGTCAGCAA CCAGGTGTGG AAAGTCCCCA GGCTCCCCAG   4440

CAGGCAGAAG TATGCAAAGC ATGCATCTCA ATTAGTCAGC AACCATAGTC CCGCCCCTAA   4500

CTCCGCCCAT CCCGCCCCTA ACTCCGCCCA GTTCCGCCCA TTCTCCGCCC CATGGCTGAC   4560

TAATTTTTTT TATTTATGCA GAGGCCGAGG CCGCCTCGGC CTCTGAGCTA TTCCAGAAGT   4620

AGTGAGGAGG CTTTTTTGGA GGCCTAGGCT TTTGCAAAAA GCTTCACGCT GCCGCAAGCA   4680

CTCAGGGCGC AAGGGCTGCT AAAGGAAGCG GAACACGTAG AAAGCCAGTC CGCAGAAACG   4740

GTGCTGACCC CGGATGAATG TCAGCTACTG GGCTATCTGG ACAAGGGAAA ACGCAAGCGC   4800

AAAGAGAAAG CAGGTAGCTT GCAGTGGGCT TACATGGCGA TAGCTAGACT GGGCGGTTTT   4860

ATGGACAGCA AGCGAACCGG AATTGCCAGC TGGGGCGCCC TCTGGTAAGG TTGGGAAGCC   4920

CTGCAAAGTA AACTGGATGG CTTTCTTGCC GCCAAGGATC TGATGGCGCA GGGGATCAAG   4980

ATCTGATCAA GAGACAGGAT GAGGATCGTT TCGCATGATT GAACAAGATG GATTGCACGC   5040

AGGTTCTCCG GCCGCTTGGG TGGAGAGGCT ATTCGGCTAT GACTGGGCAC AACAGACAAT   5100

CGGCTGCTCT GATGCCGCCG TGTTCCGGCT GTCAGCGCAG GGGCGCCCGG TTCTTTTTGT   5160

CAAGACCGAC CTGTCCGGTG CCCTGAATGA ACTGCAGGAC GAGGCAGCGC GGCTATCGTG   5220

GCTGGCCACG ACGGGCGTTC CTTGCGCAGC TGTGCTCGAC GTTGTCACTG AAGCGGGAAG   5280

GGACTGGCTG CTATTGGGCG AAGTGCCGGG GCAGGATCTC CTGTCATCTC ACCTTGCTCC   5340

TGCCGAGAAA GTATCCATCA TGGCTGATGC AATGCGGCGG CTGCATACGC TTGATCCGGC   5400

TACCTGCCCA TTCGACCACC AAGCGAAACA TCGCATCGAG CGAGCACGTA CTCGGATGGA   5460

AGCCGGTCTT GTCGATCAGG ATGATCTGGA CGAAGAGCAT CAGGGGCTCG CGCCAGCCGA   5520

ACTGTTCGCC AGGCTCAAGG CGCGCATGCC CGACGGCGAG GATCTCGTCG TGACCCATGG   5580

CGATGCCTGC TTGCCGAATA TCATGGTGGA AAATGGCCGC TTTTCTGGAT TCATCGACTG   5640

TGGCCGGCTG GGTGTGGCGG ACCGCTATCA GGACATAGCG TTGGCTACCC GTGATATTGC   5700

TGAAGAGCTT GGCGGCGAAT GGGCTGACCG CTTCCTCGTG CTTTACGGTA TCGCCGCTCC   5760

CGATTCGCAG CGCATCGCCT TCTATCGCCT TCTTGACGAG TTCTTCTGAG CGGGACTCTG   5820

GGGTT                                                               5825
```

(2) INFORMATION FOR SEQ ID NO: 8:

(i) SEQUENCE CHARACTERISTICS:
(A) LENGTH: 4023 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Influenza virus, RNA sequence
(C) INDIVIDUAL ISOLATE: pHL1490

(xi) SEQUENCE DESCRIPTION: SEQ ID NO: 8:

```
CAGGTACATA TTGAAAGATG AGTCTTCTAA CCGAGGTCGA AACGTACGTT CTCTCTATCA     60

TCCCGTCAGG CCCCCTCAAA GCCGAGATCG CACAGAGACT TGAAGATGTC TTTGCAGGGA    120
```

-continued

```
AGAACACCGA TCTTGAGGTT CTCATGGAAT GGCTAAAGAC AAGACCAATC CTGTCACCTC    180
TGACTAAGGG GATTTTAGGA TTTGTGTTCA CGCTCACCGT GCCCAGTGAG CGAGGACTGC    240
AGCGTAGACG CTTTGTCCAA AATGCCCTTA ATGGGAACGG GGATCCAAAT AACATGGACA    300
AAGCAGTTAA ACTGTATAGG AAGCTCAAGA GGGAGATAAC ATTCCATGGG GCCAAAGAAA    360
TCTCACTCAG TTATTCTGCT GGTGCACTTG CCAGTTGTAT GGGCCTCATA TACAACAGGA    420
TGGGGGCTGT GACCACTGAA GTGGCATTTG GCCTGGTATG TGCAACCTGT GAACAGATTG    480
CTGACTCCCA GCATCGGTCT CATAGGCAAA TGGTGACAAC AACCAACCCA CTAATCAGAC    540
ATGAGAACAG AATGGTTTTA GCCAGCACTA CAGCTAAGGC TATGGAGCAA ATGGCTGGAT    600
CGAGTGAGCA AGCAGCAGAG GCCATGGAGG TTGCTAGTCA GGCTAGGCAA ATGGTGCAAG    660
CGATGAGAAC CATTGGGACT CATCCTAGCT CCAGTGCTGG TCTGAAAAAT GCTCTTCTTG    720
AAAATTTGCA GGCCTATCAG AAACGAATGG GGGTGCAGAT GCAACGGTTC AAGTGATCCT    780
CTCGCTATTG CCGCAAATAT CATTGGGATC TTGCACTTGA TATTGTGGAT TCTTGATCGT    840
CTTTTTTTCA AATGCATTTA CCGTCGCTTT AAATACGGAC TGAAAGGAGG GCCTTCTACG    900
GAAGGAGTGC CAAAGTCTAT GAGGGAAGAA TATCGAAAGG AACAGCAGAG TGCTGTGGAT    960
GCTGACGATG GTCATTTTGT CAGTATAGAG CTGGAGTAAA AAGTACCTT GTTTCTACTA   1020
CCTATCTCCA GGTCCAATAG GACCAGATCT AAAAGATCAC AAGCATAAAA GAGACAGGGA   1080
GGAAAGTGAC AGGCCACAGA GAATACCTGG AAGTCATACC TGGGGAGGTG GCCCAAAAAT   1140
GACCCCATAA CGAAAAGAAC CGGACCTCAA AGGAACAACT GGTCGACCTG ACAACCCGGA   1200
GAACTGATAA GACCGACAGG TCAATGAAAG AAAACCGCGC CCATAGCTTT CCCTCGGCCT   1260
CAGACGTACA GGGCCCGCTA ACAGCGCGAT TTGCTGGTGA CCCAATGCGA CCAGATGCTC   1320
CACGCCCAGT CGCGTACCGT CTTCATGGGA GAAAATAATA CTGTTGATGG GTGTCTGGTC   1380
AGAGACATCA AGAAATAACG CCGGAACATT AGTGCAGGCA GCTTCCACAG CAATGGCATC   1440
CTGGTCATCC AGCGGATAGT TAATGATCTA CCGCGGTAGA TCTAGCCCAC TGAACGCGGG   1500
CGGCACCTCG CTAACGGATT CACCACTCCA AGAATTGGAG CCAATCAATT CTTGCGGAGA   1560
ACTGTGAATG CGCAAACCAA CCCTTGGCAG AACATATCCA TCGCGTCCGC CATCTCCAGC   1620
AGCCGCACGC GGCGCATCTC GGGCCGCGTT GCTGGCGTTT TTCCATAGGC TCCGCCCCCC   1680
TGACGAGCAT CACAAAAATC GACGCTCAAG TCAGAGGTGG CGAAACCCGA CAGGACTATA   1740
AAGATACCAG GCGTTTCCCC CTGGAAGCTC CCTCGTGCGC TCTCCTGTTC CGACCCTGCC   1800
GCTTACCGGA TACCTGTCCG CCTTTCTCCC TTCGGGAAGC GTGGCGCTTT CTCAATGCTC   1860
ACGCTGTAGG TATCTCAGTT CGGTGTAGGT CGTTCGCTCC AAGCTGGGCT GTGTGCACGA   1920
ACCCCCCGTT CAGCCCGACC GCTGCGCCTT ATCCGGTAAC TATCGTCTTG AGTCCAACCC   1980
GGTAAGACAC GACTTATCGC CACTGGCAGC AGCCACTGGT AACAGGATTA GCAGAGCGAG   2040
GTATGTAGGC GGTGCTACAG AGTTCTTGAA GTGGTGGCCT AACTACGGCT ACACTAGAAG   2100
GACAGTATTT GGTATCTGCG CTCTGCTGAA GCCAGTTACC TTCGGAAAAA GAGTTGGTAG   2160
CTCTTGATCC GGCAAACAAA CCACCGCTGG TAGCGGTGGT TTTTTTGTTT GCAAGCAGCA   2220
GATTACGCGC AGAAAAAAAG GATCTCAAGA AGATCCTTTG ATCTTTTCTA CGGGGTCTGA   2280
CGCTCAGTGG AACGAAAACT CACGTTAAGG GATTTTGGTC ATGAGATTAT CAAAAAGGAT   2340
CTTCACCTAG ATCCTTTTAA ATTAAAAATG AAGTTTTAAA TCAATCTAAA GTATATATGA   2400
GTAAACTTGG TCTGACAGTT ACCAATGCTT AATCAGTGAG GCACCTATCT CAGCGATCTG   2460
```

-continued

```
TCTATTTCGT TCATCCATAG TTGCCTGACT CCCCGTCGTG TAGATAACTA CGATACGGGA   2520
GGGCTTACCA TCTGGCCCCA GTGCTGCAAT GATACCGCGA GACCCACGCT CACCGGCTCC   2580
AGATTTATCA GCAATAAACC AGCCAGCCGG AAGGGCCGAG CGCAGAAGTG GTCCTGCAAC   2640
TTTATCCGCC TCCATCCAGT CTATTAATTG TTGCCGGGAA GCTAGAGTAA GTAGTTCGCC   2700
AGTTAATAGT TTGCGCAACG TTGTTGCCAT TGCTGCAGGC ATCGTGGTGT CACGCTCGTC   2760
GTTTGGTATG GCTTCATTCA GCTCCGGTTC CCAACGATCA AGGCGAGTTA CATGATCCCC   2820
CATGTTGTGC AAAAAAGCGG TTAGCTCCTT CGGTCCTCCG ATCGTTGTCA GAAGTAAGTT   2880
GGCCGCAGTG TTATCACTCA TGGTTATGGC AGCACTGCAT AATTCTCTTA CTGTCATGCC   2940
ATCCGTAAGA TGCTTTTCTG TGACTGGTGA GTACTCAACC AAGTCATTCT GAGAATAGTG   3000
TATGCGGCGA CCGAGTTGCT CTTGCCCGGC GTCAACACGG GATAATACCG CGCCACATAG   3060
CAGAACTTTA AAAGTGCTCA TCATTGGAAA ACGTTCTTCG GGGCGAAAAC TCTCAAGGAT   3120
CTTACCGCTG TTGAGATCCA GTTCGATGTA ACCCACTCGT GCACCCAACT GATCTTCAGC   3180
ATCTTTTACT TTCACCAGCG TTTCTGGGTG AGCAAAAACA GGAAGGCAAA ATGCCGCAAA   3240
AAAGGGAATA AGGGCGACAC GGAAATGTTG AATACTCATA CTCTTCCTTT TTCAATATTA   3300
TTGAAGCATT TATCAGGGTT ATTGTCTCAT GAGCGGATAC ATATTTGAAT GTATTTAGAA   3360
AAATAAACAA AAGAGTTTGT AGAAACGCAA AAAGGCCATC CGTCAGGATG GCCTTCTGCT   3420
TAATTTGATG CCTGGCAGTT TATGGCGGGC GTCCTGCCCG CCACCCTCCG GGCCGTTGCT   3480
TCGCAACGTT CAAATCCGCT CCCGGCGGAT TTGTCCTACT CAGGAGAGCG TTCACCGACA   3540
AACAACAGAT AAAACGAAAG GCCCAGTCTT TCGACTGAGC CTTTCGTTTT ATTTGATGCC   3600
TGGCAGTTCC CTACTCTCGC ATGGGGAGAC CCCACACTAC CATCGGCGCT ACGGCGTTTC   3660
ACTTCTGAGT TCGGCATGGG GTCAGGTGGG ACCACCGCGC TACTGCCGCC AGGCAAATTC   3720
TGTTTTATCA GACCGCTTCT GCGTTCTGAT TTAATCTGTA TCAGGCTGAA AATCTTCTCT   3780
CATCCGCCAA AACAGAAGCT AGCGGCCGCT AGCTTGGGCT GCAGGTCGAC TCTAGAGGAT   3840
CCCCAAAAAA AAAAAAAAAA AAAAAAAAAA GAGTCCAGAG TGGCCCCGCC GTTCCGCGCC   3900
GGGGGGGGGG GGGGGGGGGG ACACTTTCGG ACATCTGGTC GACCTCCAGC ATCGGGGGAA   3960
AAAAAAAAAA CAAAGTTTCG CCCGGAGTAC TGGTCGACCT CCGAAGTTGG GGGGGAGTAG   4020
AAA                                                                 4023
```

(2) INFORMATION FOR SEQ ID NO: 9:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (iv) ANTI-SENSE: NO (vi) ORIGINAL SOURCE:
(A) ORGANISM: Influenza virus, vRNA 3' sequence
(B) INDIVIDUAL ISOLATE: pHL1104 vRNA Promoter Element (xi) SEQUENCE DESCRIPTION: SEQ ID NO: 9:

```
CCUGUUUCUA CU                                                       12
```